(12) United States Patent
Johnson et al.

(10) Patent No.: US 9,096,526 B2
(45) Date of Patent: Aug. 4, 2015

(54) PROCESSES FOR THE PREPARATION OF 4-AMINO-3-HALO-6-(SUBSTITUTED) PICOLINATES AND 4-AMINO-5-FLUORO-3-HALO-6-(SUBSTITUTED)PICOLINATES

(71) Applicants: Peter L. Johnson, Indianapolis, IN (US); James M. Renga, Indianapolis, IN (US); Natalie C. Giampietro, Carmel, IN (US); Gregory T. Whiteker, Carmel, IN (US); Christopher Galliford, Indianapolis, IN (US)

(72) Inventors: Peter L. Johnson, Indianapolis, IN (US); James M. Renga, Indianapolis, IN (US); Natalie C. Giampietro, Carmel, IN (US); Gregory T. Whiteker, Carmel, IN (US); Christopher Galliford, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/104,236

(22) Filed: Dec. 12, 2013

(65) Prior Publication Data
US 2014/0171654 A1 Jun. 19, 2014

Related U.S. Application Data

(60) Provisional application No. 61/736,830, filed on Dec. 13, 2012.

(51) Int. Cl.
*C07D 213/72* (2006.01)
*C07D 213/74* (2006.01)
*C07D 213/73* (2006.01)
*C07D 251/12* (2006.01)

(52) U.S. Cl.
CPC .......... *C07D 213/74* (2013.01); *C07D 213/73* (2013.01); *C07D 251/12* (2013.01)

(58) Field of Classification Search
None
See application file for complete search history.

(56) References Cited

U.S. PATENT DOCUMENTS 6,784,137 B2 8/2004 Balko et al.
7,314,849 B2 1/2008 Balko et al.
7,432,227 B2 10/2008 Balko et al.

OTHER PUBLICATIONS

CAPLUS 2003:837044.*

* cited by examiner

*Primary Examiner* — Heidi Reese
(74) *Attorney, Agent, or Firm* — Michael R. Asam

(57) ABSTRACT

4-Amino-3-chloro-6-(substituted)picolinates are prepared from difluoroacetic acid or trifluoroacetic acid, tritylamine or t-butylamine as a protecting group, a 3,3-dialkoxyprop-1-yne and a substituted methylene amine by a series of steps.

6 Claims, No Drawings

PROCESSES FOR THE PREPARATION OF 4-AMINO-3-HALO-6-(SUBSTITUTED) PICOLINATES AND 4-AMINO-5-FLUORO-3-HALO-6-(SUBSTITUTED) PICOLINATES

CROSS REFERENCE TO RELATED APPLICATIONS

This application claims the benefit of U.S. Provisional Patent Application Ser. No. 61/736,830 filed Dec. 13, 2012, the disclosure of which is expressly incorporated herein by reference.

FIELD

Provided herein are processes for the preparation of 4-amino-5-fluoro-3-halo-6-(substituted)picolinates and 4-amino-3-halo-6-(substituted)picolinates. More particularly, provided herein are processes for the preparation of 4-amino-5-fluoro-3-halo-6-(substituted)picolinates and 4-amino-3-halo-6-(substituted)picolinates from a non-pyridine source.

BACKGROUND

U.S. Pat. No. 6,784,137 B2 and U.S. Pat. No. 7,314,849 B2 describe inter alia certain 4-amino-5-fluoro-3-halo-6-(aryl)picolinate and 4-amino-3-halo-6-(aryl)picolinate compounds and their use as herbicides. U.S. Pat. No. 7,432,227 B2 describes inter alia certain 4-amino-5-fluoro-3-halo-6-(alkyl)picolinate and 4-amino-3-halo-6-(alkyl)picolinate compounds and their use as herbicides. Each of these patents describes the manufacture of 4-amino-5-fluoro-3-halopicolinate starting materials by fluorination of the corresponding 5-unsubstituted pyridines with 1-(chloromethyl)-4-fluoro-1,4-diazoniabicyclo[2.2.2]octane bis(tetrafluoroborate). Each of these patents also describes the manufacture of 4-amino-6-(aryl)picolinates from coupling reactions involving picolines having either a facile leaving group or a metal derivative in the 6-position of the picoline ring. It would be advantageous to produce 4-amino-5-fluoro-3-halo-6-(substituted)picolinates and 4-amino-3-halo-6-(substituted)picolinates without having to rely on metal-assisted couplings. It would be advantageous to produce 4-amino-5-fluoro-3-halo-6-(substituted)picolinates and 4-amino-3-halo-6-(substituted)picolinates efficiently and in high yield from a non-pyridine source. It would also be advantageous to produce 4-amino-5-fluoro-3-halo-6-(substituted)picolinates without having to rely on direct fluorination of the 5-position of the pyridine ring with an expensive fluorinating agent like 1-(chloromethyl)-4-fluoro-1,4-diazoniabicyclo[2.2.2]octane bis(tetrafluoroborate).

SUMMARY

Provided herein are processes for the preparation of 4-amino-3-halo-5-fluoro-6-(substituted)picolinates and 4-amino-3-halo-6-(substituted)picolinates from a non-pyridine source without a metal-assisted coupling and without fluorination with an expensive fluorinating agent like 1-(chloromethyl)-4-fluoro-1,4-diazoniabicyclo[2.2.2]octane bis(tetrafluoroborate). More particularly, provided herein are processes for the preparation of a 4-amino-3-halo-6-(substituted)picolinate of the Formula I

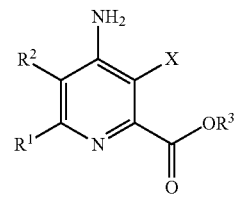

wherein

X represents Cl, Br or I, $R^1$ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, $R^2$ represents H or F, and $R^3$ represents $C_1$-$C_{12}$ alkyl or an unsubstituted or substituted $C_7$-$C_{11}$ arylalkyl, which comprises the following steps:

a) contacting difluoroacetic acid or trifluoroacetic acid with tritylamine or t-butylamine in the presence of a triarylphosphine and a trialkylamine base in carbon tetrachloride solvent to produce a 2,2-difluoro- or 2,2,2-trifluoro-N-(trityl or t-butyl)ethanimidoyl chloride (Formula A)

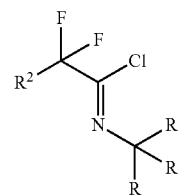

wherein each R represents $CH_3$ or each R represents $C_6H_5$, and $R^2$ represents H or F;

b) contacting the 2,2-difluoro- or 2,2,2-trifluoro-N-(trityl or t-butyl)ethanimidoyl chloride (Formula A) with a 3,3-dialkoxyprop-1-yne (Formula B)

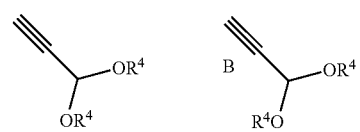

wherein $R^4$ represents $C_1$-$C_4$ alkyl, in the presence of copper(I) iodide, an alkali metal iodide and an alkali metal phosphate in a polar aprotic solvent to produce an (imino)pent-2-yne dialkyl acetal of Formula C

C

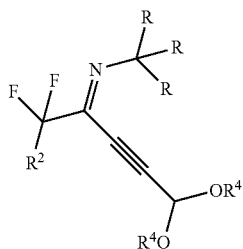

wherein R, R² and R⁴ are as previously defined;
c) cyclizing the (imino)pent-2-yne dialkyl acetal of Formula C with an amine of Formula D

D

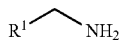

wherein R¹ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, in the presence of an inorganic alkali metal base in a polar aprotic solvent at a temperature from about ambient to about 100° C. to produce a trityl- or t-butyl-protected 4-amino-6-(substituted)pyridine-2-dialkyl acetal of Formula E

E

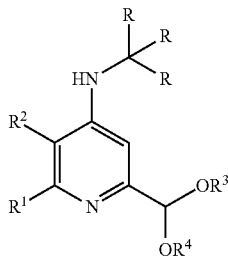

wherein R, R¹, R² and R⁴ are as previously defined;
d) deprotecting and hydrolyzing the trityl- or t-butyl-protected 4-amino-6-(substituted) pyridine-2-dialkyl acetal of the Formula E with a mineral acid in a polar solvent to produce the 4-amino-6-(substituted)picolinaldehyde of the Formula F

F

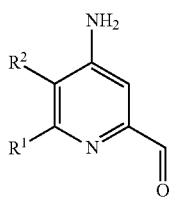

wherein R¹ and R² are as previously defined;
e) oxidizing the 4-amino-6-(substituted)picolinaldehyde of the Formula F with an alkali metal chlorite in the presence of an inorganic acid and a hypochlorous acid scavenger in an aqueous alcoholic solvent to produce a 4-amino-6-(substituted)picolinic acid of the Formula G

G

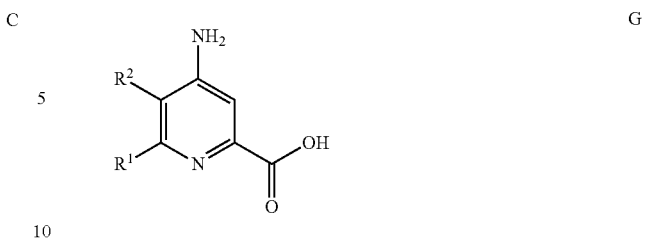

wherein R¹ and R² are as previously defined;
f) esterifying the 4-amino-6-(substituted)picolinic acid of the Formula G with a compound of the formula

R³Y wherein
Y represents OH, Cl, Br, or I, and
R³ represents $C_1$-$C_{12}$ alkyl or an unsubstituted or substituted $C_7$-$C_{11}$ arylalkyl,
to produce a 4-amino-6-(substituted)picolinate of Formula H

H

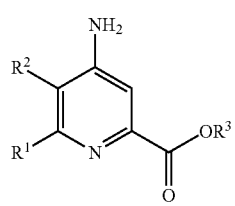

wherein R¹, R² and R³ are as previously defined; and
g) halogenating the 4-amino-6-(substituted)picolinate of Formula H with a halogen source to produce the 4-amino-3-halo-6-(substituted)picolinate of Formula I.

The halogenation (step g)) may also be performed on the aldehyde immediately after step d). Thus, provided herein are also processes for the preparation of a 4-amino-3-halo-6-(substituted)picolinate of the Formula I

I

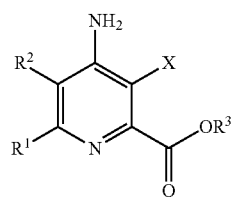

wherein
X represents Cl, Br or I,
R¹ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy,
R² represents H or F, and
R³ represents $C_1$-$C_{12}$ alkyl or an unsubstituted or substituted $C_7$-$C_{11}$ arylalkyl, which comprises the following steps:
a) contacting difluoroacetic acid or trifluoroacetic acid with tritylamine or t-butylamine in the presence of a triarylphosphine and a trialkylamine base in carbon tetrachloride solvent to produce a 2,2-difluoro- or 2,2,2-trifluoro-N-(trityl or t-butyl)ethanimidoyl chloride (Formula A)

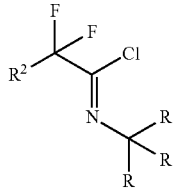
A wherein
each R represents CH$_3$ or each R represents C$_6$H$_5$, and R$^2$ represents H or F;

b) contacting the 2,2-difluoro- or 2,2,2-trifluoro-N-(trityl or t-butyl)ethanimidoyl chloride (A) with a 3,3-dialkoxyprop-1-yne (Formula B)

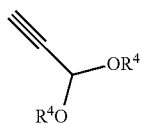
B wherein R$^4$ represents C$_1$-C$_4$ alkyl,
in the presence of copper (I) iodide, alkali metal iodide and alkali metal phosphate in a polar aprotic solvent to produce an (imino)pent-2-yne dialkyl acetal of Formula C

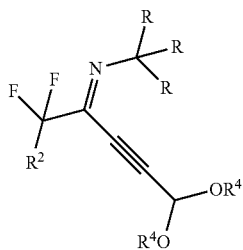
C wherein R, R$^2$ and R$^4$ are as previously defined;

c) cyclizing the (imino)pent-2-yne dialkyl acetal of Formula C with an amine of Formula D

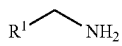
D wherein
R$^1$ represents H, C$_1$-C$_6$ alkyl, C$_3$-C$_6$ cycloalkyl, C$_4$-C$_6$ cycloalkylalkyl, C$_3$-C$_6$ heterocycle, C$_2$-C$_4$ alkenyl or phenyl, arylalkyl or heteroarylalkyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy,
in the presence of an inorganic alkali metal base in a polar aprotic solvent at a temperature from about ambient to about 100° C. to produce a trityl- or t-butyl-protected 4-amino-6-(substituted)pyridine-2-dialkyl acetal of Formula E

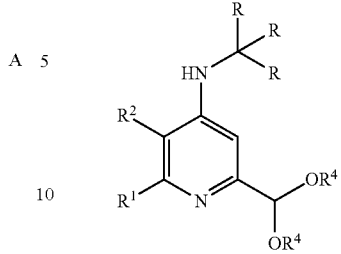
E wherein R, R$^1$, R$^2$ and R$^4$ are as previously defined;

d) deprotecting and hydrolyzing the trityl- or t-butyl-protected 4-amino-6-(substituted) pyridine-2-dialkyl acetal of the Formula E with a mineral acid in a polar solvent to produce the 4-amino-6-(substituted)picolinaldehyde of the Formula F

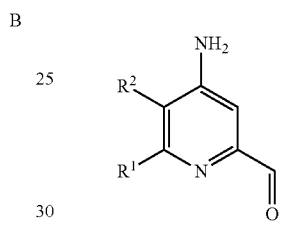
F wherein R$^1$ and R$^2$ are as previously defined;

e) halogenating the 4-amino-6-(substituted)picolinaldehyde of Formula F with a halogen source to produce the 4-amino-3-halo-6-(substituted)picolinaldehyde of Formula J

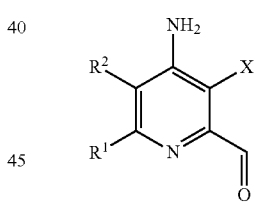
J wherein R$^1$, R$^2$ and X are as previously defined;

f) oxidizing the 4-amino-3-halo-6-(substituted)picolinaldehyde of Formula J with an alkali metal chlorite in the presence of an inorganic acid and a hypochlorous acid scavenger in an aqueous alcoholic solvent to produce a 4-amino-3-halo-6-(substituted)picolinic acid of the Formula K

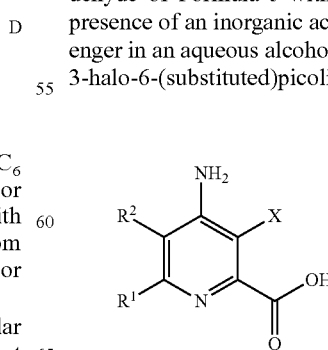
K wherein $R^1$, $R^2$ and X are is as previously defined; and g) esterifying the 4-amino-3-halo-6-(substituted)picolinic acid of the Formula K with a compound of the formula $$R^3Y \qquad 5$$

wherein

Y represents OH, Cl, Br, or I, and $R^3$ represents $C_1$-$C_{12}$ alkyl or an unsubstituted or substituted $C_7$-$C_{11}$ arylalkyl, to produce the 4-amino-3-halo-6-(substituted)picolinate of Formula I.

Another embodiment is the compound of Formula A wherein each R represents $CH_3$ or each R represents $C_6H_5$, and $R^2$ represents H or F.

Another embodiment is a compound of Formula C wherein each R represents $CH_3$ or each R represents $C_6H_5$, and $R^2$ represents H or F, and $R^4$ represents $C_1$-$C_4$ alkyl.

Another embodiment is a compound of Formula E wherein $R^1$ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, each R represents $CH_3$ or each R represents $C_6H_5$, $R^2$ represents H or F, and $R^4$ represents $C_1$-$C_4$ alkyl.

Another embodiment is a compound of Formula F wherein $R^1$ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and $R^2$ represents H or F.

DETAILED DESCRIPTION

The terms "alkyl" and "alkenyl," as well as derivative terms such as "alkoxy," as used herein, include within their scope straight chain and branched chain moieties.

The term "arylalkyl," as used herein, refers to a phenyl substituted alkyl group having a total of 7 to 11 carbon atoms, such as benzyl ($-CH_2C_6H_5$), 2-methylnaphthyl ($-CH_2C_{10}H_7$) and 1- or 2-phenethyl ($-CH_2CH_2C_6H_5$ or $-CH(CH_3)C_6H_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, $C(O)OC_1$-$C_6$ alkyl, or where two adjacent substituents are taken together as $-O(CH_2)_n-O-$ wherein n=1 or 2, provided that the substituents are sterically compatible and the rules of chemical bonding and strain energy are satisfied.

Unless specifically limited otherwise, the term "halogen," as well as derivative terms such as "halo," refers to fluorine, chlorine, bromine and iodine.

The phenyl groups substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy may be of any orientation, but 4-substituted phenyl, 2,4-disubstituted phenyl, 2,3,4-trisubstituted phenyl, 2,4,5-trisubstituted phenyl, and 2,3,4,6-tetrasubstituted phenyl isomers are preferred.

The term "heterocycle," as used herein, refers to a ring containing 3-6 carbon atoms and at least one N, O or S atom, such as pyridine, thiazole or tetrahydrofuranyl. The heterocycle can be unsubstituted or substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy of any orientation. The heterocycle can be saturated, partially unsaturated or aromatic.

The term "heteroarylalkyl," as used herein, refers to a heterocycle substituted alkyl group having a total of 4 to 10 carbon atoms, such as thiazol-2-ylmethyl ($-CH_2C_3H_2NS$) or thiophen-2-ylmethyl ($-CH_2C_4H_3S$).

4-Amino-5-fluoro-3-chloro-6-(substituted)picolinates are prepared from trifluoroacetic acid, tritylamine, a 3,3-dialkoxyprop-1-yne and a substituted methylene amine by a series of steps.

a) 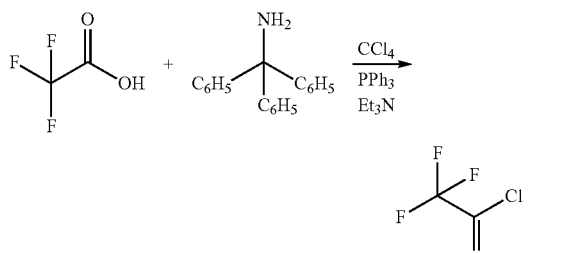

b) 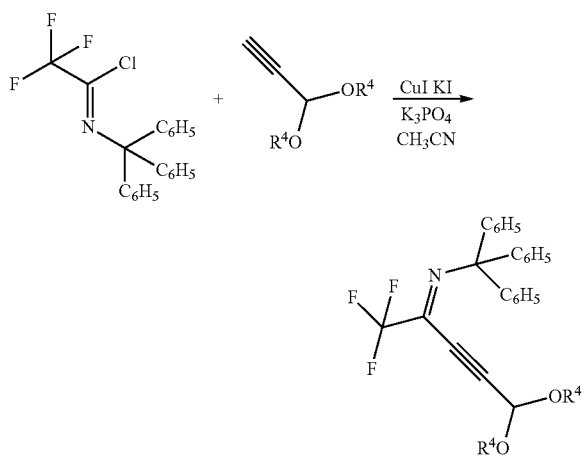

c) 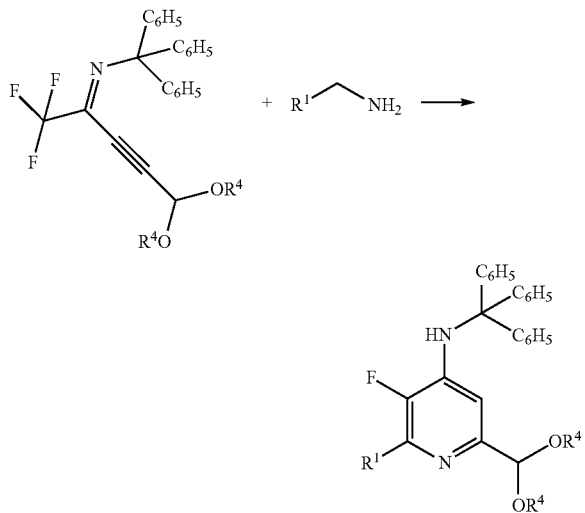

d) 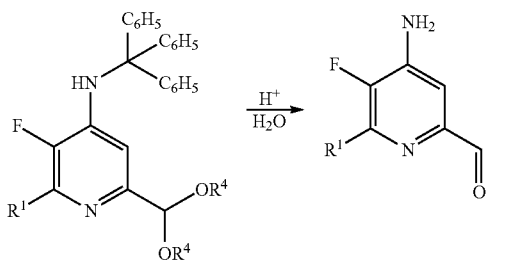

e), f), g) 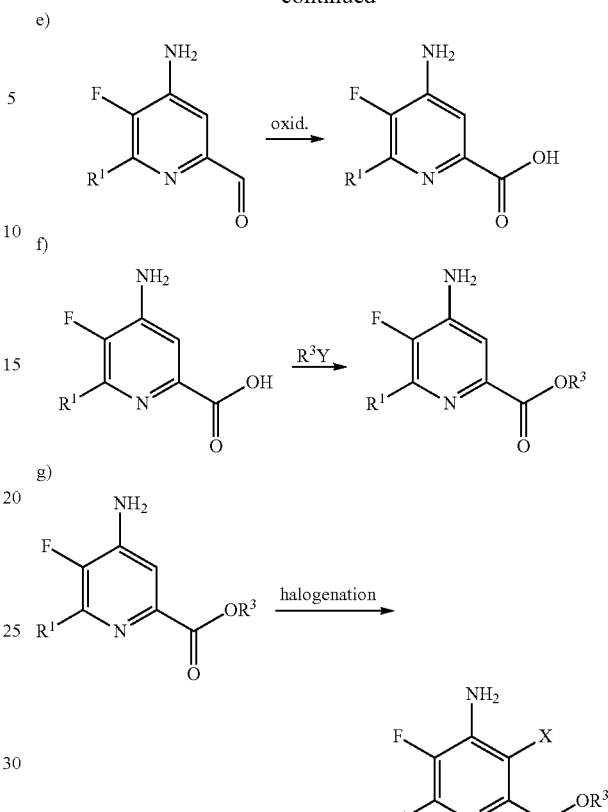

4-Amino-3-chloro-6-(substituted)picolinates are similarly prepared from difluoroacetic acid, tritylamine, a 3,3-dialkoxyprop-1-yne and a substituted methylene amine.

For both 4-amino-5-fluoro-3-chloro-6-(substituted)picolinates and 4-amino-3-chloro-6-(substituted)picolinates, the tritylamine protecting group can be replaced by a t-butylamine protecting group.

In step a), trifluoroacetic acid is reacted with tritylamine and carbon tetrachloride in the presence of a triarylphosphine and a trialkylamine base to produce 2,2,2-trifluoro-N-(trityl)ethanimidoyl chloride. While one equivalent of tritylamine is required for each equivalent of trifluoroacetic acid, it is often convenient to use an excess of the tritylamine, typically a 10 to 20% excess. A similar excess of trialkylamine base is also preferred. It is often convenient to use a much larger excess of triarylphosphine, typically in the range of a 2 to 4 fold excess. Carbon tetrachloride, while serving as a reactant, is also conveniently used as a solvent for the initial reaction. The reaction is exothermic and it is convenient to control the exotherm by external cooling and the controlled addition of a carbon tetrachloride solution of tritylamine to a mixture of trifluoroacetic acid, trialkylamine and triarylphosphine in carbon tetrachloride. After the initial exotherm subsides, the reaction mixture is generally heated to reflux until the conversion is complete.

In a typical reaction, a mixture of about 3 equivalents of triphenylphosphine and trifluoroacetic acid in carbon tetrachloride are cooled to about 0° C. in an ice bath and a 20% excess of triethylamine is added. With continued cooling, about a 20% excess of tritylamine in carbon tetrachloride is slowly added. After completion of the addition, the mixture is heated to about 70° C. for several hours. After cooling, the reaction mixture is extracted with hexane and the solvent evaporated to provide crude 2,2,2-trifluoro-N-(trityl)-ethanimidoyl chloride.

In step b), the 2,2,2-trifluoro-N-(trityl)ethanimidoyl chloride is coupled with a 3,3-dialkoxyprop-1-yne in the presence of copper (I) iodide, an alkali metal iodide and an alkali metal phosphate in a polar aprotic solvent to produce an N-(5,5-dialkoxy-1,1,1-trifluoropent-3-yn-2-ylidene)-1,1,1-triphenylmethanamine. While one equivalent of 3,3-dialkoxyprop-1-yne is required for each equivalent of ethanimidoyl chloride, it is often convenient to use an excess of the 3,3-dialkoxyprop-1-yne, typically a 10 to 20% excess. Similarly, a 10 to 20% molar excess of alkali metal iodide and alkali metal phosphate are generally preferred. While the reaction is catalytic in copper (I) iodide, usually about 0.1 to about 0.3 equivalents are employed. The coupling reaction is conducted in a polar aprotic solvent at a temperature from about 40° C. to about 100° C. Preferred polar aprotic solvents include ethers like tetrahydrofuran, esters like ethyl acetate, nitriles like acetonitrile, amides like N,N-dimethylformamide and N-methylpyrrolidinone and sulfoxides like dimethyl sulfoxide. Anhydrous solvents are preferred with anhydrous acetonitrile being especially preferred.

In a typical reaction, 2,2,2-trifluoro-N-(trityl)ethanimidoyl chloride and a slight excess of 3,3-diethoxyprop-1-yne are mixed with about 0.3 equivalents of copper (I) iodide and slight excesses of potassium phosphate and potassium iodide in anhydrous acetonitrile. The mixture is heated at about 60° C. under a nitrogen atmosphere until the reaction is complete. After cooling, an extraction solvent like a halogenated hydrocarbon is added to the mixture along with water. The organic layer is recovered, washed with brine and dried. The solvent is evaporated to provide crude N-(5,5-diethoxy-1,1,1-trifluoropent-3-yn-2-ylidene)-1,1,1-triphenylmethanamine.

In step c), the N-(5,5-dialkoxy-1,1,1-trifluoropent-3-yn-2-ylidene)-1,1,1-triphenylmethanamine is reacted with a methylene amine substituted with a H, an alkyl, a cycloalkyl, an alkenyl or a (substituted)phenyl, an arylalkyl or a heteroarylalkyl group in the presence of an inorganic alkali metal base in a polar aprotic solvent to produce a trityl-protected 4-amino-5-fluoro-6-(substituted)pyridine dialkyl acetal. While one equivalent of substituted methylene amine is required for each equivalent of N-(5,5-dialkoxy-1,1,1-trifluoropent-3-yn-2-ylidene)-1,1,1-triphenylmethanamine, it is often convenient to use an excess of the substituted methylene amine, typically a 2 to 4 fold excess. Suitable inorganic alkali metal bases include the lithium, sodium, potassium and cesium salts of hydroxides, carbonates and phosphates. Cesium carbonate is particularly preferred. In general, it is convenient to use a 2 to 4 fold excess of the inorganic alkali metal base. Preferred polar aprotic solvents include ethers like tetrahydrofuran, esters like ethyl acetate, nitriles like acetonitrile, amides like N,N-dimethylformamide and N-methylpyrrolidinone and sulfoxides like dimethyl sulfoxide. Anhydrous solvents are preferred with anhydrous tetrahydrofuran and dimethyl sulfoxide being especially preferred. The reaction is typically conducted at a temperature from about ambient to about 100° C.

In a typical reaction, N-(5,5-diethoxy-1,1,1-trifluoropent-3-yn-2-ylidene)-1,1,1-triphenylmethanamine is mixed with about a 2.5 to 3 fold excess of (4-chloro-2-fluoro-3-methoxyphenyl)methyl amine and about a 2.5 to 3 fold excess of cesium carbonate in anhydrous tetrahydrofuran. The mixture is heated at about 80° C. until the reaction is complete. After cooling, an extraction solvent like a halogenated hydrocarbon is added to the mixture along with water. The organic layer is recovered, washed with brine and dried. The solvent is evaporated to provide crude 2-(4-chloro-2-fluoro-3-methoxyphenyl)-6-(diethoxymethyl)-3-fluoro-N-tritylpyridin-4-amine.

In step d), the trityl-protected 4-amino-5-fluoro-6-(substituted)pyridine-2-dialkyl acetal is treated with a mineral acid in a polar solvent at a temperature from about ambient to about 100° C. to produce a 4-amino-5-fluoro-6-(substituted) picolinaldehyde. Suitable mineral acids include sulfuric and phosphoric acids with sulfuric acid being preferred. The mineral acids are usually used as aqueous solutions. Approximately one equivalent of mineral acid is required but a 10 to 30% excess is preferred. The deprotection/hydrolysis is conveniently performed in a mixture of a polar solvent such as acetonitrile with water.

In a typical reaction, 2-(4-chloro-2-fluoro-3-methoxyphenyl)-6-(diethoxymethyl)-3-fluoro-N-tritylpyridin-4-amine is treated with a 1 M (molar) solution of sulfuric acid in a mixture of acetonitrile-water. The mixture is heated at reflux until the reaction is complete. The mixture is added to methylene chloride, and the organic layer is separated, washed with brine and dried. The solvent is evaporated to provide crude 4-amino-6-(4-chloro-2-fluoro-3-methoxyphenyl)-5-fluoropicolinaldehyde.

In step e), the 4-amino-5-fluoro-6-(substituted)picolinaldehyde is oxidized with an alkali metal chlorite in the presence of an inorganic acid salt and a hypochlorous acid scavenger in an aqueous organic solvent mixture to produce a 4-amino-5-fluoro-6-(substituted)picolinic acid. While one equivalent of sodium chlorite is required for the oxidation of the aldehyde to the carboxylic acid, it is often convenient to use 2-8 equivalents. The oxidation occurs in mixtures of water with organic solvents such as acetonitrile or t-butanol under slightly acidic conditions (pH 3-5), achieved by the addition of 2-10 equivalents of inorganic acid salts such as disodium hydrogen phosphate. To avoid unwanted reactions from the hypochlorous acid formed during the oxidation, 2-30 equivalents of a scavenger such as 2-methyl-2-butene, resorcinol or sulfamic acid is added.

In a typical reaction, 4-amino-6-(4-chloro-2-fluoro-3-methoxyphenyl)-5-fluoropicolinaldehyde is oxidized with an excess of sodium chlorite, between 20-30 equivalents of 2-methyl-2-butene and about 5 equivalents of disodium hydrogen phosphate in a t-butanol/water mixture. The mixture is heated at about 80° C. until the reaction is complete. After cooling, the mixture is treated with dilute hydrochloric acid and extracted with ethyl acetate. The organic layer is separated and dried. The solvent is evaporated to provide crude 4-amino-6-(4-chloro-2-fluoro-3-methoxyphenyl)-5-fluoropicolinic acid.

In step f), the 4-amino-5-fluoro-6-(substituted)picolinic acid is esterified. Esters of the picolinic acids are prepared by coupling of the picolinic acid with an alcohol using any number of suitable activating agents such as those used for peptide couplings such as dicyclohexylcarbodiimide (DCC) or carbonyl diimidazole (CDI) or by reacting the corresponding acid with an appropriate arylalkyl alcohol in the presence of an acid catalyst. Alternatively, the esters can be prepared by reacting the picolinic acid with an alkyl or arylalkyl halide in the presence of a base. These procedures are well known to organic chemists and are described, for example, in U.S. Patent Application Publication 2012/0190551 A1

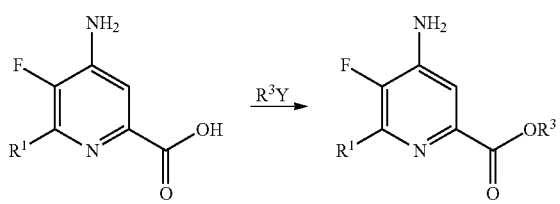

In a typical reaction, 4-amino-6-(4-chloro-2-fluoro-3-methoxyphenyl)-5-fluoropicolinic acid is reacted with a slight excess of benzyl bromide and about 2 equivalents of potassium carbonate in a polar aprotic solvent such as dimethyl sulfoxide or N,N-dimethylformamide (DMF). Benzyl 4-amino-6-(4-chloro-2-fluoro-3-methoxyphenyl)-5-fluoropicolinate is recovered by partitioning the reaction mixture between ethyl acetate and water, separating and drying the organic phase and evaporating the solvent.

In step g), the 4-amino-5-fluoro-6-(substituted)picolinate is halogenated with a halogen source to produce the 4-amino-5-fluoro-3-halo-6-(substituted)picolinate of Formula I. In the halogenation reaction, a chlorine, bromine or iodine atom is introduced into the 3-position of the picolinate by reacting the 3-unsubstituted picolinate with a halogen source in an inert solvent.

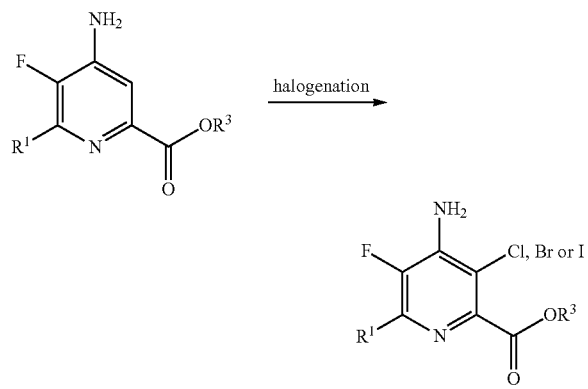

When the halogen atom at the 3-position is Cl, the chlorine source can be chlorine ($Cl_2$) itself or reagents such as sulfuryl chloride, N-chlorosuccinimide or 1,3-dichloro-5,5-dimethylimidazolidine-2,4-dione. When chlorine or sulfuryl chloride is used, a large excess of chlorinating agent is used. When chlorine gas is used, the reaction is performed in an inert solvent, preferably, a solvent such as dichloromethane, dichloromethane-water or acetic acid. When sulfuryl chloride is used, the reaction can be performed in an inert solvent, such as dichloromethane or in neat sulfuryl chloride. The temperature at which the reaction is conducted is not critical but usually is from about 0° C. to about 45° C. and preferably from about 10° C. to about 30° C. A typical reaction generally requires from about 0.5 to about 5 hours. The chlorination reaction is usually conducted at ambient atmospheric pressure.

When the chlorinating agent used is N-chlorosuccinimide or 1,3-dichloro-5,5-dimethylimidazolidine-2,4-dione, the reaction is carried out using a stoichiometric amount of chlorinating reagent. For chlorinations using 1,3-dichloro-5,5-dimethylimidazolidine-2,4-dione as the chlorinating agent, both chlorines in the hydantoin are found to react. The reaction is performed in an inert polar solvent, such as DMF or acetonitrile. The temperature at which the reaction is conducted is not critical but usually is from about 20° C. to about 85° C. and preferably from about 50° C. to about 80° C. When acetonitrile is used as solvent, it is convenient to carry out the reaction at the reflux temperature. A typical reaction generally requires from about 0.5 to about 5 hours. The chlorination reaction is usually conducted at ambient atmospheric pressure.

When the halogen atom at the 3-position is Br, the bromine source can be bromine ($Br_2$) itself or reagents such as sulfuryl bromide, N-bromosuccinimide or 1,3-dibromo-5,5-dimethylimidazolidine-2,4-dione. When $Br_2$ is used as the brominating agent, a large excess can be employed, and the reaction is performed in an inert solvent, preferably, a solvent such as dichloromethane, dichloromethane-water or acetic acid. The temperature at which the reaction is conducted is not critical but usually is from about 0° C. to about 45° C. and preferably from about 10° C. to about 30° C. A typical reaction generally requires from about 0.5 to about 5 hours. The bromination reaction is usually conducted at ambient atmospheric pressure.

When the brominating agent used is N-bromosuccinimide or 1,3-dibromo-5,5-dimethylimidazolidine-2,4-dione, the reaction is carried out using a stoichiometric amount of brominating reagent. The reaction is performed in an inert polar solvent, such as DMF or acetonitrile. The temperature at which the reaction is conducted is not critical but usually is from about 20° C. to about 85° C. and preferably from about 50° C. to about 80° C. When acetonitrile is used as solvent, it is convenient to carry out the reaction at the reflux temperature. A typical reaction generally requires from about 0.5 to about 5 hours. The bromination reaction is usually conducted at ambient atmospheric pressure.

When the halogen atom at the 3-position is I, the iodine source can be iodine ($I_2$) itself or reagents such as iodine monochloride or N-iodosuccinimide Periodic acid may be used in conjunction with $I_2$. When $I_2$ is used as the iodinating agent, a large excess of $I_2$ can be employed, and the reaction is performed in an inert solvent, preferably, a solvent such as dichloromethane, dichloromethane-water, methyl alcohol or acetic acid. The temperature at which the reaction is conducted is not critical but usually is from about 0° C. to about 45° C. and preferably from about 10° C. to about 30° C. A typical reaction generally requires from about 0.5 to about 5 hours. The iodination reaction is usually conducted at ambient atmospheric pressure.

In a typical reaction, benzyl 4-amino-6-(4-chloro-2-fluoro-3-methoxyphenyl)-5-fluoropicolinate is treated with 0.55 equivalents of 1,3-dichloro-5,5-dimethylimidazolidine-2,4-dione in acetonitrile. The reaction mixture is stirred at reflux for 1 hour. After cooling to room temperature, water is added to precipitate the product.

In those cases where the halogenating agent does not react with an aldehyde functionality, the halogenation (step g) may also be performed on the aldehyde of Formula F.

The products obtained by any of these processes, can be recovered by conventional means, such as evaporation or extraction, and can be purified by standard procedures, such as by recrystallization or chromatography.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

The terms picolinate, picolinaldehyde and picolinic acid can also be expressed as pyridine-2-carboxylate, pyridine-2-carbaldehyde and pyridine-2-carboxylic acid, respectively.

Example 1

2,2,2-Trifluoro-N-(trityl)ethanimidoyl chloride

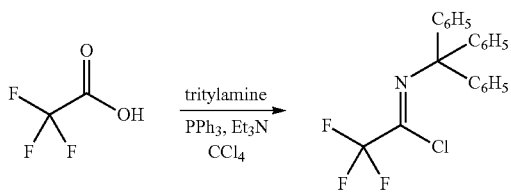

A 1-liter (L), three neck round bottom flask equipped with a mechanical stirrer, addition funnel and J-KEM temperature probe was charged with tritylamine (24.90 grams (g), 96 millimoles (mmol), Alfa Aesar) and carbon tetrachloride (150 milliliters (mL)). The solution was cooled in an ice bath (<5° C.) and treated in portions with trifluoroacetic acid (6.13 mL, 80 mmol). The addition was done at such rate to keep the temperature ≤10° C. Once the mixture had cooled back below 5° C., it was treated dropwise with triethylamine (13.4 mL, 96 mmol, no exotherm). Once the addition of triethylamine was complete, the ice bath was removed, the addition funnel was replaced with a reflux condenser and the reaction mixture was heated to 65° C. using a heating mantle. Triphenylphosphine ($Ph_3P$; 62.9 g, 240 mmol) was then added portionwise (5-10 g at a time). With each addition of triphenyphosphine the temperature would initially drop 2-3° C. and then rise to ~70° C. The reaction mixture was allowed to cool to 65-66° C. before additional $Ph_3P$ was added (precipitate formed in the reaction mixture, $Ph_3P=O$). Once all of the triphenylphosphine had been added, the reaction mixture was heated to 76° C.

After stirring at 76° C. for ~2 hours (h) the reaction mixture was allowed to cool to room temperature and was treated with hexanes (400 mL). After rapidly stirring for ~30 minutes (min), the mixture was filtered through a Buchner funnel. The collected solid was re-suspended in hexanes (400 mL), and the suspension was stirred for several minutes and filtered. The filtrates were combined and concentrated in vacuo to give a solid. The solid was slurried with hexanes (~300 mL) and filtered through filter paper. The filtrate, a yellow solution, was concentrated in vacuo to give 14.32 g of a light yellow solid. The solids that were removed by filtration were combined and stirred hexanes (500 mL). TLC analysis of the hexanes phase showed what appeared to be product. The mixture was filtered, and the solids were once again stirred with hexanes (500 mL). The solids were removed by vacuum filtration through a fritted glass funnel. The filtrate was combined with the 14.32 g of light yellow solid. The solvent was removed in vacuo to give 30.37 g of a light yellow solid. The crude material was crystallized from acetonitrile (~250 mL); crystals formed upon cooling). After standing in a freezer for 2 h, the crystals were removed by vacuum filtration and washed with cold acetonitrile. The material was air-dried for several minutes and then dried in a vacuum oven (40-50° C.) to give the title product (21.97 g, 73%) as fine, white needles: mp 144-145° C.; $^1H$ NMR (400 MHz, $CDCl_3$) δ 7.34-7.19 (m, 15H); $^{19}F$ NMR (376 MHz, $CDCl_3$) δ −71.24; EIMS m/z 373 ($M^+$), 338, 296, 243, 219, 193, 165, 143, 127, 119, 77; IR (thin film) 3070, 1712, 1488, 1444, 1270, 1162, 1151, 946, 770 $cm^{-1}$.

Example 2

2,2-Difluoro-N-(trityl)ethanimidoyl chloride

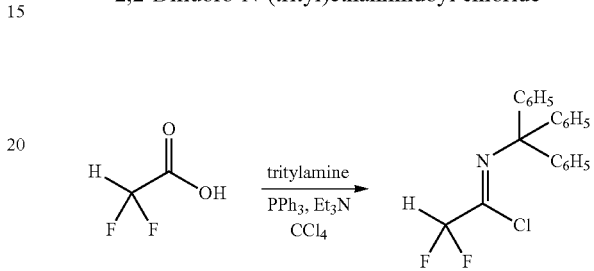

A 1-L, three neck round bottom flask equipped with a mechanical stirrer, addition funnel and J-KEM temperature probe was charged with tritylamine (24.90 g, 96 mmol, Alfa Aesar) and carbon tetrachloride (150 mL). The solution was cooled in an ice bath (<5° C.) and treated in portions with difluoroacetic acid (5.03 mL, 80 mmol). The addition was done at such rate to keep the temperature ≤10° C. Once the mixture had cooled back below 5° C. it was treated dropwise with triethylamine (13.4 mL, 96 mmol, no exotherm). Once the addition of triethylamine was complete, the ice bath was removed, the addition funnel was replaced with a reflux condenser, and the reaction mixture was heated to 65° C. using a heating mantle. Triphenylphosphine ($Ph_3P$; 62.9 g, 240 mmol) was then added portionwise (5-10 g at a time). With each addition of triphenyphosphine the temperature would initially drop 2-3° C. and then rise to ~70° C. The reaction mixture was allowed to cool to 65-66° C. before additional $Ph_3P$ was added (precipitate formed in the reaction mixture, $Ph_3P=O$). Once all of the triphenylphosphine had been added, the reaction mixture was heated to 76° C.

After stirring at 76° C. for 2 h, the reaction mixture was allowed to cool to room temperature and was treated with hexanes (400 mL). After rapidly stirring for ~30 min, the mixture was filtered through a Buchner funnel. The collected solid was re-suspended in hexanes (400 mL) warmed to 50° C. and the suspension was stirred for several minutes and filtered. (This process was repeated four times; by the fifth time there appeared to be no desired product in the hexanes.) The hexane extracts were filtered through filter paper and concentrated in vacuo to give 29.09 g of a light tan solid. The crude material was recrystallized from acetonitrile (~250 mL). After standing overnight in a freezer, the crystals were removed by vacuum filtration and washed with cold acetonitrile. The solid was air-dried for several hours and then dried in a vacuum oven (40-50° C., high vacuum) to give 2,2-difluoro-N-(trityl)-ethanimidoyl chloride (17.83 g, 63%) as a cream colored solid: mp 154-156° C.; $^1H$ NMR (400 MHz, CDCl$_3$) δ 7.39-7.09 (m, 15H), 6.22 (t, J=55.4 Hz, 1H); $^{19}$F NMR (376 MHz, CDCl$_3$) δ −117.50.

Example 3

N-tert-Butyl-2,2,2-trifluoroethanimidoyl chloride

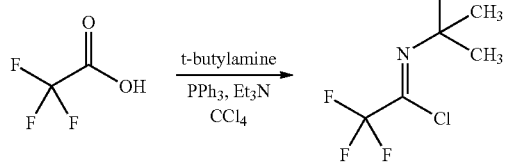

A 1-L, three neck round bottom flask equipped with a mechanical stirrer, addition funnel and J-KEM temperature probe was charged with t-butylamine (31.5 mL, 0.30 moles (mol)) and carbon tetrachloride (200 mL). The solution was cooled in an ice bath (<5° C.) and treated in one portion with trifluoroacetic acid (19 mL, 0.25 mol, exotherm to 60° C. along with white precipitate formation). Once the mixture had cooled back below 5° C., it was treated dropwise with triethylamine (42 mL, 0.30 mol, no exotherm). Once the addition was complete, the ice bath was removed, the addition funnel was replaced with a reflux condenser, and the reaction mixture was heated to 65° C. via heating mantle. Triphenylphosphine (192 g, 1.248 mol) was then added portionwise (10-20 g at a time). Very little, in any, exotherm was observed until ~75% of the triphenylphosphine had been added. At this point the temperature very gradually rose above 70° C. (became homogeneous) at which point a very vigorous exotherm occurred and the temperature rapidly rose above 80° C. The exotherm was controlled by occasionally cooling in an ice bath. Once the exotherm had subsided (white precipitate formed) the remaining triphenylphosphine was added portionwise. Once all of the triphenylphosphine had been added the reaction mixture was heated to 76° C.

After stirring at 76° C. for ~2 h, the reaction mixture was allowed to cool to room temperature and was treated with hexanes (500 mL). After rapidly stirring for ~30 min, the mixture was filtered through a Buchner funnel. The collected solid was re-suspended in hexanes (500 mL), and the suspension was stirred for several minutes and filtered. The filtrate was concentrated in vacuo (house vac., bath temp <10° C.). A lot of solids were present. The residue was treated with pentane and filtered. The solvent was removed in vacuo (house vac., bath temp <10° C.) to give 9.23 g of a dark yellow liquid. The crude material was distilled using a short path distillation head. N-tert-Butyl-2,2,2-trifluoroethanimidoyl chloride (5.84 g, 13%) was isolated as a colorless liquid: bp 35-44° C. (103 mmHg); $^1$H NMR (400 MHz, CDCl$_3$) δ 1.42 (s, 9H). EIMS m/z 187 (M$^+$), 172, 157, 136, 117, 69, 57.

Example 4

N-(5,5-Diethoxy-1,1,1-trifluoropent-3-yn-2-ylidene-1,1,1-triphenylmethanamine

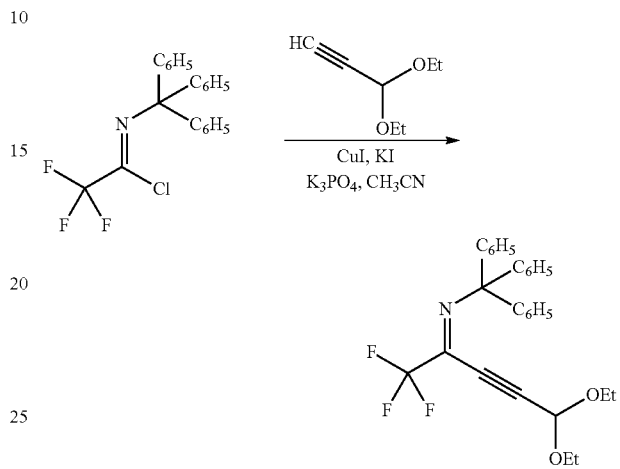

A 500 mL, three neck round bottom flask equipped with a mechanical stirrer, reflux condenser and J-KEM temperature probe was charged with propargylaldehyde diethyl acetal (5.13 g, 40 mmol), anhydrous acetonitrile (Aldrich Sure/Seal™; 125 mL) and 2,2,2-trifluoro-N-(trityl)ethanimidoyl chloride (14.95 g, 40 mmol). Potassium iodide (KI; 6.64 g, 40 mmol), potassium phosphate (K$_3$PO$_4$; 11.04 g, 52 mmol) and copper(I) iodide (CuI; 2.29 g, 12 mmol) were combined and ground to a fine powder with a mortar and pestle and then added to the reaction mixture. Additional acetonitrile (25 mL) was added, and the resultant mixture was warmed to 60° C. using a heating mantle under a atmosphere of N$_2$. After stirring overnight at 60° C., an aliquot of the reaction mixture was partitioned between ethyl acetate (EtOAc) and water (H$_2$O) and analyzed by thin layer chromatography (TLC; 95/5 hexanes/EtOAc) and gas chromatography-mass spectrometry (GC-MS). Both methods showed imidoyl chloride staring material still present along with one major product and the dimer of the alkyne. The reaction mixture was treated with an addition 20 mole percent (mol %) of the following reagents: propargylaldehyde diethyl acetal (1 g), KI (1.33 g), CuI (0.56 g) and K$_3$PO$_4$ (2.20 g). The temperature of the reaction mixture was raised to 70° C.

After an additional 3 h at 70° C., TLC and GC-MS still show imidoyl chloride starting material remaining After ~24 h total, the reaction mixture was allowed to cool to room temperature, diluted with dichloromethane (CH$_2$Cl$_2$; 400 mL), filtered through filter paper and washed with H$_2$O (1×150 mL) and saturated aqueous sodium chloride (NaCl; 1×150 mL). The organic phase was dried (sodium sulfate; Na$_2$SO$_4$), filtered and concentrated in vacuo to give 22.02 g of a yellow oil (which solidified upon standing in a refrigerator). The crude material was dissolved in warm hexanes, loaded onto a silica gel column and purified by chromatography using the following setup: Teledyne-Isco CombiFlash Companion, 330 g RediSep silica gel column, flow=100 mL/min, detection at 254 nanometers (nm), solvent A=hexanes, solvent B=CH$_2$Cl$_2$. A linear gradient was used starting at 100% A (6 min) and going to 60% B over a period of 50 min. Very good separation was achieved with this system, although the desired product slowly came off the column in >60 fractions. Fractions containing the major product were combined and concentrated in vacuo to give the desired product (12.11 g, 65%) as a white solid: mp 84-86° C.; $^1$H NMR (400 MHz, CDCl$_3$) δ 7.45-7.04 (m, 15H), 4.88 (d, J=1.2 Hz, 1H), 3.39 (m, 4H), 1.13 (td, J=7.1, 1.2 Hz, 6H); $^{19}$F NMR (376 MHz, CDCl$_3$) δ −71.29; EIMS m/z 465 (M+), 436, 394, 366, 346, 243, 165, 103, 75.

Example 5

N-(5,5-diethoxy-1,1-difluoropent-3-yn-2-ylidene)-1,1,1-triphenylmethanamine

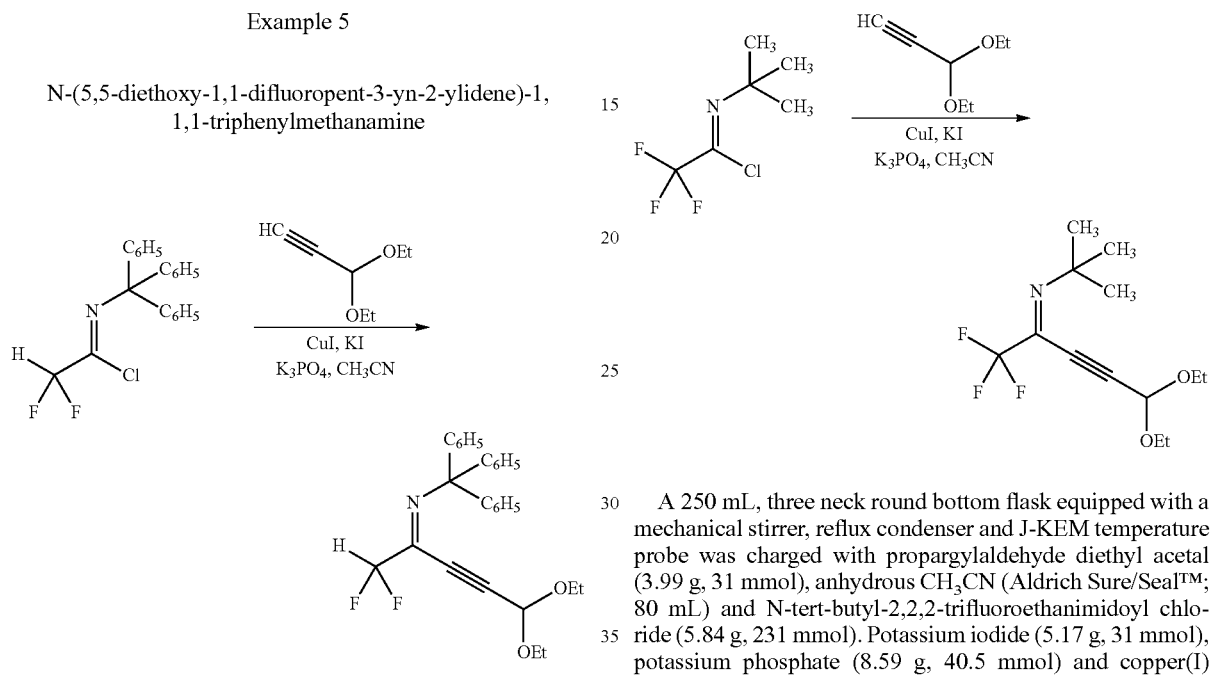

A mixture of 2,2-difluoro-N-(trityl)ethanimidoyl chloride (2.80 g, 7.87 mmol) in anhydrous acetonitrile (CH$_3$CN; 30 mL) was treated with propargylaldehyde diethyl acetal (1.1 mL, 7.87 mmol). Potassium iodide (1.31 g, 7.87 mmol), potassium phosphate (2.17 g, 10.23 mmol) and copper(I) iodide (0.45 g, 2.36 mmol) were combined and ground to a fine powder with a mortar and pestle and then added to the reaction mixture. The reaction mixture was placed in an oil bath and heated to 60° C.

After 2 h at 60° C., an aliquot of the reaction mixture was partitioned between EtOAc and H$_2$O and analyzed by TLC (90/10 hexanes/EtOAc). TLC analysis indicated that all of the imidoyl chloride had been consumed. The reaction mixture was allowed to cool to room temperature, diluted with EtOAc (75 mL) and washed with H$_2$O (2×25 mL) and saturated NaCl (1×25 mL). The organic phase was dried (Na$_2$SO$_4$), filtered and concentrated in vacuo to give 3.46 g of a yellow paste. The crude material was dissolved in hexanes/EtOAc, loaded onto a silica gel column and purified by chromatography using the following setup: Teledyne-Isco CombiFlash Companion, 80 g RediSep silica gel column, flow=60 mL/min, detection at 254 nm, solvent A=hexanes, solvent B=EtOAc. A linear gradient was used starting at 100% A (2 min) and going to 30% B over a period of 20 min N-(5,5-Diethoxy-1,1-difluoropent-3-yn-2-ylidene)-1,1,1-triphenylmethanamine (2.230 g, 63%) was isolated as a white solid: mp 173-175° C.; $^1$H NMR (400 MHz, CDCl$_3$) δ 7.33-7.13 (m, 15H), 6.21 (t, J=55.8 Hz, 1H), 4.90 (s, 1H), 3.39 (qq, J=9.5, 7.1 Hz, 4H), 1.13 (t, J=7.1 Hz, 6H); $^{19}$F NMR (376 MHz, CDCl$_3$) δ −117.88 (s); EIMS m/z 447 (M+), 418, 402, 376, 348, 328, 243, 165, 115, 103, 75.

Example 6

N-(5,5-Diethoxy-1,1,1-trifluoropent-3-yn-2-ylidene)-2-methylpropan-2-amine

A 250 mL, three neck round bottom flask equipped with a mechanical stirrer, reflux condenser and J-KEM temperature probe was charged with propargylaldehyde diethyl acetal (3.99 g, 31 mmol), anhydrous CH$_3$CN (Aldrich Sure/Seal™; 80 mL) and N-tert-butyl-2,2,2-trifluoroethanimidoyl chloride (5.84 g, 231 mmol). Potassium iodide (5.17 g, 31 mmol), potassium phosphate (8.59 g, 40.5 mmol) and copper(I) iodide (1.78 g, 9.34 mmol) were combined and ground to a fine powder with a mortar and pestle and then added to the reaction mixture. The resultant yellow mixture was warmed to 60° C. using a heating mantle under an atmosphere of nitrogen (N$_2$).

After stirring overnight (16 h) at 60° C., an aliquot of the reaction mixture was partitioned between EtOAc and H$_2$O and analyzed by TLC (80/20 hexanes/EtOAc) and GC-MS. TLC analysis showed a minor amount of the alkyne starting material present and one major product formed. By GC-MS it appeared that the major product had the correct mass for the desired product (very weak M+). The reaction mixture was allowed to cool to room temperature, diluted with CH$_2$Cl$_2$ (300 mL) and washed with H$_2$O (1×100 mL) and saturated NaCl (1×100 mL). The organic phase was dried (Na$_2$SO$_4$), filtered and concentrated in vacuo to give 6.91 g of a dark yellow oil.

The crude material was dissolved in hexanes, loaded onto a silica gel column and purified by chromatography using the following setup: Teledyne-Isco CombiFlash Companion, 220 g RediSep silica gel column, flow=100 mL/min, detection at 254 nm, solvent A=hexanes, solvent B=EtOAc. A linear gradient was used starting at 100% A (5 min) and going to 20% B over a period of 35 min. This procedure failed to cleanly separate the major and minor product. Fractions containing the major product were combined and concentrated in vacuo to give 5.342 g of a colorless liquid. The mixture isolated from Column-1 (5.342 g) was dissolved in hexanes, loaded onto a silica gel column and purified by chromatography using the following setup: Teledyne-Isco CombiFlash Companion, 120 g RediSep silica gel column, flow=85 mL/min, detection at 254 nm, solvent A=hexanes, solvent B=CH$_2$Cl$_2$. A linear gradient was used starting at 100% A (3 min) and going to 40% B over a period of 35 min and then to 100% B over a period of 5 minutes and held at 100% B for 10 min N-(5,5-Diethoxy-1,1,1-trifluoropent-3-yn-2-ylidene)-2-methylpropan-2-amine (4.507 g, 52%) was isolated as a colorless liquid: $^1$H NMR (400 MHz, CDCl$_3$) δ 5.44 (s, 1H), 3.74 (dq, J=9.5, 7.1 Hz, 2H), 3.64 (dq, J=9.5, 7.1 Hz, 2H), 1.42 (s, 9H), 1.25 (t, J=7.1 Hz, 6H); EIMS m/z 279 (M$^+$), 264, 234, 190, 177, 150, 108, 57; IR (thin film) 2978, 2936, 1646.351, 1316, 1201, 1132, 1053, 1022, 715 cm$^{-1}$.

Example 7

2-(4-Chloro-2-fluoro-3-methoxyphenyl)-6-(diethoxymethyl)-3-fluoro-N-tritylpyridin-4-amine

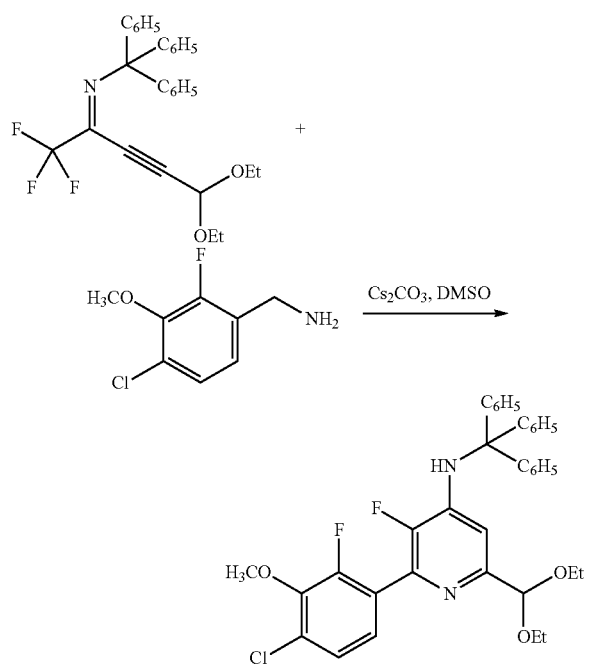

A 100 mL round bottom flask equipped with a magnetic stir bar was charged with N-(5,5-diethoxy-1,1,1-trifluoropent-3-yn-2-ylidene)-1,1,1-triphenylmethanamine (2.33 g, 5 mmol) and anhydrous dimethyl sulfoxide (DMSO, Aldrich Sure/Seal; 25 mL) under an atmosphere of N$_2$. Once all of the alkyne had dissolved, 4-chloro-2-fluoro-3-methoxybenzyl amine (2.84 g, 15 mmol, 3 equivalents (equiv)) was added to the solution. The resultant light yellow solution was stirred for 2 min at room temperature and then treated in one portion with cesium carbonate (4.07 g, 12.5 mmol, 2.5 equiv). The reaction flask was placed in an oil bath that had been pre-heated to 80° C. After 2 h at 80° C., an aliquot of the reaction mixture was partitioned between EtOAc and H$_2$O and analyzed by TLC (80/20 hexanes/EtOAc). TLC analysis indicated that all of the alkyne starting material had been consumed and one major product formed. The reaction mixture was allowed to cool to room temperature, diluted with EtOAc (150 mL) and washed with H$_2$O (3×50 mL) and saturated NaCl (1×50 mL). The organic phase was dried (Na$_2$SO$_4$), filtered and concentrated in vacuo to give 4.63 g of an orange solid.

The crude material was dissolved in CH$_2$Cl$_2$, loaded onto a silica gel column and re-purified by chromatography using the following setup: Teledyne-Isco CombiFlash Companion, 80 g RediSep silica gel column, flow=60 mL/min, detection at 254 nm, solvent A=hexanes, solvent B=EtOAc. A linear gradient was used starting at 100% A (2 min) and going to 60% B over a period of 20 min. 2-(4-Chloro-2-fluoro-3-methoxyphenyl)-6-(diethoxymethyl)-3-fluoro-N-tritylpyridin-4-amine (2.243 g, 73%) was isolated as a peach colored solid: mp 177-180° C.; $^1$H NMR (400 MHz, CDCl$_3$) δ 7.37-7.19 (m, 17H), 6.34 (d, J=6.5 Hz, 1H), 5.90 (d, J=4.5 Hz, 1H), 5.09 (s, 1H), 3.98 (d, J=1.0 Hz, 3H), 3.30 (dq, J=9.4, 7.1 Hz, 2H), 3.16 (dq, J=9.4, 7.0 Hz, 2H), 1.03 (t, J=7.0 Hz, 6H); $^{19}$F NMR (376 MHz, CDCl$_3$) δ −128.23 (d, J=33.8 Hz), −146.89 (d, J=33.1 Hz); HRMS-ESI (m/z) [M+H]$^+$ calcd for C$_{36}$H$_{33}$ClF$_2$N$_2$O$_3$, 614.2148. found, 614.2156.

Example 8

2-(4-Chlorophenyl)-6-(diethoxymethyl)-3-fluoro-N-tritylpyridin-4-amine

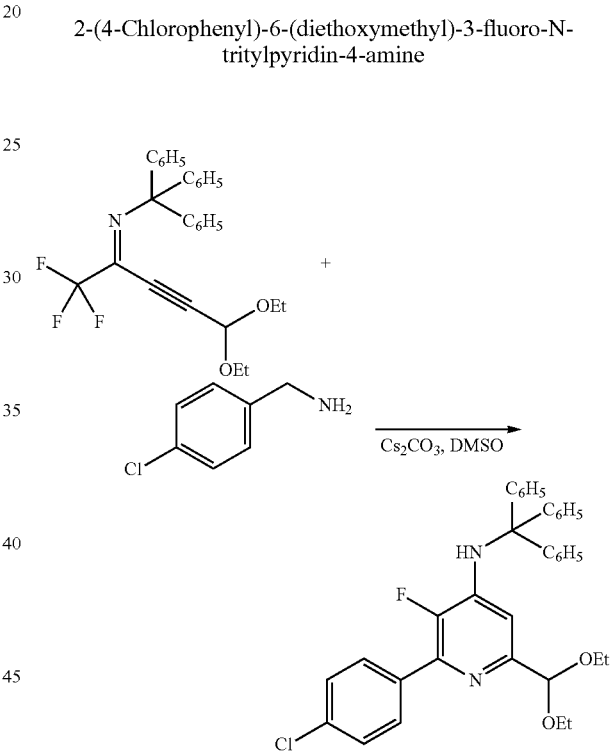

A 25 mL round bottom flask equipped with a magnetic stir bar and reflux condenser was charged with the N-(5,5-diethoxy-1,1,1-trifluoropent-3-yn-2-ylidene)-1,1,1-triphenylmethanamine (931 mg, 2 mmol) and anhydrous DMSO (Aldrich Sure/Seal™; 10 mL). Once all of the alkyne had dissolved, 4-chlorobenzylamine (0.73 mL, 6 mmol) was added (solution went from colorless to light yellow), followed by cesium carbonate (1.63 g, 5 mmol, slight warming). The resultant mixture was placed in an oil bath that had been pre-heated to 80° C. After stirring at 80° C. for 2 h, an aliquot of the reaction mixture was partitioned between EtOAc and H$_2$O and analyzed by TLC (90/10 hexanes/EtOAc) and liquid chromatography-mass spectrometry (LC-MS). TLC analysis indicated that all of the alkyne starting material had been consumed.

The reaction mixture was allowed to cool to room temperature, diluted with EtOAc (75 mL), and washed with H$_2$O (3×25 mL) and saturated NaCl (1×25 mL). The organic phase was dried (Na$_2$SO$_4$), filtered and concentrated in vacuo to give 1.69 g of a yellow oil. The crude material was dissolved in hexanes, loaded onto a silica gel column and purified by chromatography using the following setup: Teledyne-Isco CombiFlash Companion, 80 g RediSep silica gel column, flow=60 mL/min, detection at 254 nm, solvent A=hexanes, solvent B=EtOAc. A linear gradient was used starting at 100% A (5 min) and going to 30% B over a period of 20 min Fractions containing clean major product were combined and concentrated in vacuo. The residual oil was treated with hexanes and concentrated (3×~5 mL) to give the title compound (914 mg, 81%) as a light tan solid: mp 143-145° C.; $^1$H NMR (400 MHz, CDCl$_3$) δ 7.94-7.81 (m, 2H), 7.44-7.36 (m, 2H), 7.36-7.18 (m, 15H), 6.28 (d, J=6.3 Hz, 1H), 5.89 (d, J=4.8 Hz, 1H), 5.10 (s, 1H), 3.30 (dq, J=9.4, 7.0 Hz, 2H), 3.17 (dq, J=9.4, 7.0 Hz, 2H), 1.03 (t, J=7.0 Hz, 6H); $^{19}$F NMR (376 MHz, CDCl$_3$) δ −150.09 (s); HRMS-ESI (m/z) [M+H]$^+$ calcd for C$_{35}$H$_{32}$ClFN$_2$O$_2$, 566.2136. found, 566.2124.

Example 9

6-(Diethoxymethyl)-3-fluoro-2-propyl-N-tritylpyridin-4-amine

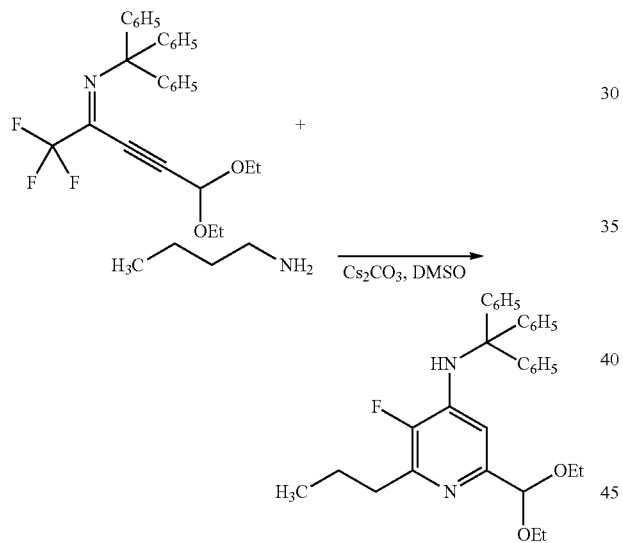

To a magnetically stirred solution of N-(5,5-diethoxy-1,1,1-trifluoropent-3-yn-2-ylidene)-1,1,1-triphenylmethanamine (4.66 g, 10 mmol) in anhydrous DMSO (30 mL) at room temperature was added n-butylamine (2.97 mL, 30.0 mmol) over 2 min. The temperature rose to 30° C. and the reaction mixture was stirred for 30 min. To the light yellow solution was added cesium carbonate (8.15 g, 25.00 mmol) and the reaction mixture was heated to 100° C. for 16 h.

Upon cooling to room temperature the orange reaction mixture was added to EtOAc (100 mL) and H$_2$O (100 mL). The aqueous layer was washed with EtOAc (100 mL), and the combined organic layers were washed with water (3×100 mL), a saturated solution of NaCl (100 mL) and dried (MgSO$_4$). Solvent removal gave 5.34 g of a viscous yellow oil. Flash column chromatography on silica gel eluting with 10% EtOAc/hexane gave 6-(diethoxymethyl)-3-fluoro-2-propyl-N-tritylpyridin-4-amine (4.21 g, 83%) as a near colorless glass, which crystallized: mp 111-112° C.; $^1$H NMR (400 MHz, CDCl$_3$) δ 7.27 (m, 15H), 6.15 (d, J=6.6 Hz, 1H), 5.72 (d, J=4.4 Hz, 1H), 5.03 (s, 1H), 3.25 (dq, J=9.4, 7.1 Hz, 2H), 3.12 (dq, J=9.4, 7.0 Hz, 2H), 2.71 (ddd, J=9.1, 7.0, 2.9 Hz, 2H), 1.69 (h, J=7.4 Hz, 2H), 1.00 (t, J=7.1 Hz, 6H), 0.95 (d, J=7.4 Hz, 3H); $^{13}$C NMR (101 MHz, CDCl$_3$) δ 151.88 (d, J=5.9 Hz), 147.12 (d, J=244.6 Hz), 146.37 (d, J=14.6 Hz), 144.28, 140.57 (d, J=9.7 Hz), 128.90, 128.19, 127.19, 107.52, 102.28, 71.16, 61.21, 33.66, 22.32, 15.06, 14.00; $^{19}$F NMR (376 MHz, CDCl$_3$) δ −152.53 (dd, J=6.1, 3.4 Hz); HRMS-ESI (m/z) [M+H]$^+$ calcd for C$_{32}$H$_{35}$FN$_2$O$_2$, 498.268. found, 498.2683.

2-(tert-Butyl)-6-(diethoxymethyl)-3-fluoro-N-tritylpyridin-4-amine

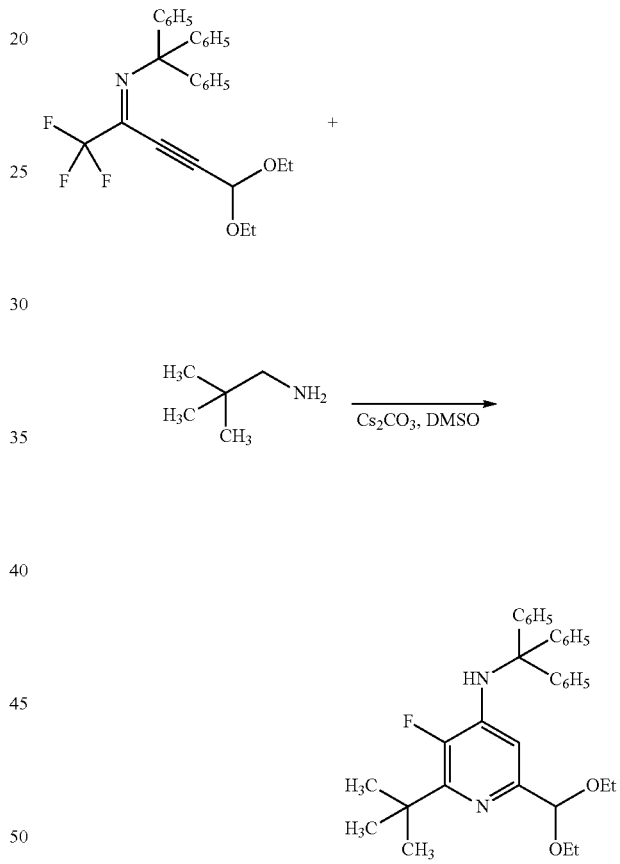

Using the procedure of Example 9, N-(5,5-diethoxy-1,1,1-trifluoropent-3-yn-2-ylidene)-1,1,1-triphenylmethanamine (2.328 g, 5 mmol), cesium carbonate (4.07 g, 12.50 mmol), 2,2-dimethylpropan-1-amine (1.307 g, 15.00 mmol) and anhydrous DMSO (20 mL) gave 2-(tert-butyl)-6-(diethoxymethyl)-3-fluoro-N-tritylpyridin-4-amine (2.61 g, 97%) as an off-white solid: mp 168-169.5° C.; $^1$H NMR (400 MHz, CDCl$_3$) δ 7.28 (m, 15H), 6.16 (d, J=6.1 Hz, 1H), 5.71 (d, J=5.2 Hz, 1H), 5.01 (s, 1H), 3.29 (dd, J=9.5, 7.1 Hz, 2H), 3.17 (dq, J=9.4, 7.0 Hz, 2H), 1.36 (d, J=1.3 Hz, 9H), 1.01 (t, J=7.0 Hz, 6H); $^{13}$C NMR (101 MHz, CDCl$_3$) δ 151.67 (d, J=9.9 Hz), 150.42 (d, J=5.9 Hz), 147.83 (d, J=249.5 Hz), 144.45, 141.00 (d, J=10.3 Hz), 128.91, 128.14, 127.12, 107.63, 102.63, 71.04, 61.35, 36.75 (d, J=5.1 Hz), 29.00 (d,

2-(Cyclopropylmethyl)-6-(diethoxymethyl)-3-fluoro-N-tritylpyridin-4-amine

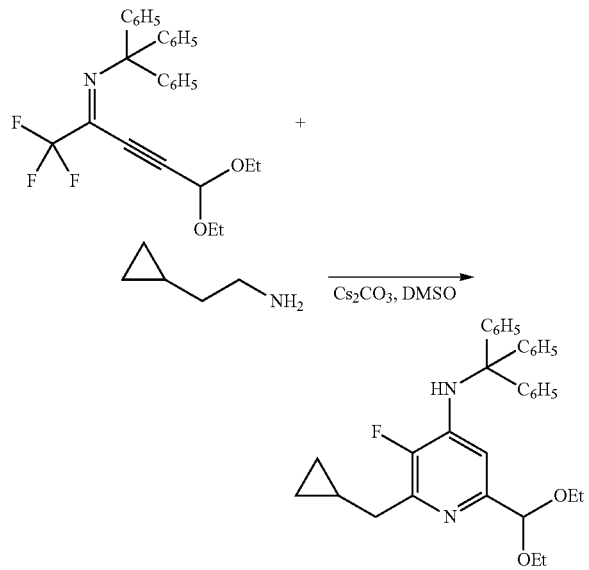

Using the procedure of Example 9, N-(5,5-diethoxy-1,1,1-trifluoropent-3-yn-2-ylidene)-1,1,1-triphenylmethanamine (4.66 g, 10 mmol), 2-cyclopropylethanamine (1.277 g, 15.00 mmol), cesium carbonate (8.15 g, 25.00 mmol) and DMSO (30 mL) gave 5.2 g of a viscous orange oil, which crystallized. Recrystallization from ether/hexane gave 2-(cyclopropylmethyl)-6-(diethoxymethyl)-3-fluoro-N-tritylpyridin-4-amine (4.53 g, 87%) as a light tan solid: mp 120-121° C.; $^1$H NMR (400 MHz, CDCl$_3$) δ 7.28 (m, 15H), 6.17 (d, J=6.6 Hz, 1H), 5.73 (d, J=4.4 Hz, 1H), 5.04 (s, 1H), 3.26 (dq, J=9.4, 7.1 Hz, 2H), 3.13 (dq, J=9.4, 7.0 Hz, 2H), 2.67 (dd, J=6.8, 2.8 Hz, 2H), 1.12 (m, 1H), 1.01 (t, J=7.0 Hz, 6H), 0.45 (m, 2H), 0.25 (m, 2H); $^{13}$C NMR (101 MHz, CDCl$_3$) δ 151.89 (d, J=5.9 Hz), 147.06 (d, J=259.0 Hz), 145.92, 144.28, 140.65 (d, J=9.8 Hz), 128.90, 128.19, 127.20, 107.66, 102.28, 71.16, 61.22, 36.47, 15.06, 10.52, 4.54; $^{19}$F NMR (376 MHz, CDCl$_3$) δ −152.19; HRMS-ESI (m/z) [M+H]$^+$ calcd for C$_{33}$H$_{35}$FN$_2$O$_2$, 510.2683. found, 510.2691.

2-Cyclobutyl-6-(diethoxymethyl)-3-fluoro-N-tritylpyridin-4-amine

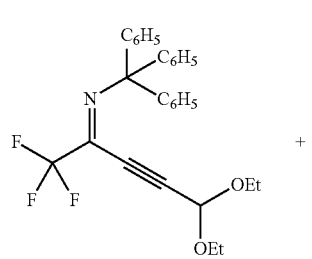

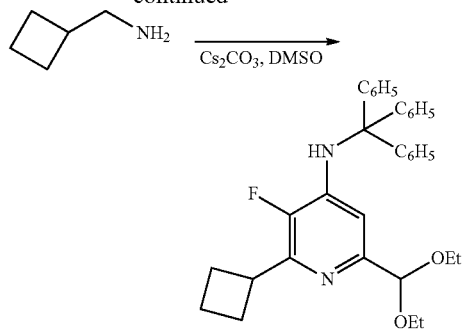

Using the procedure of Example 9, N-(5,5-diethoxy-1,1,1-trifluoropent-3-yn-2-ylidene)-1,1,1-triphenylmethanamine (2.79 g, 6 mmol), cyclobutylmethanamine hydrochloride (0.803 g, 6.60 mmol), cesium carbonate (7.82 g, 24.00 mmol) and DMSO (30 mL) gave 3.1 g of an orange solid. Column chromatography on silica gel eluting with 5% EtOAc/hexane gave 2-cyclobutyl-6-(diethoxymethyl)-3-fluoro-N-tritylpyridin-4-amine (2.44 g, 78%) as an off-white solid: mp 121-122° C.; $^1$H NMR (400 MHz, CDCl$_3$) δ 7.26 (m, 15H), 6.13 (d, J=6.5 Hz, 1H), 5.68 (d, J=4.4 Hz, 1H), 5.06 (s, 1H), 3.80 (m, 1H), 3.27 (dq, J=9.4, 7.1 Hz, 2H), 3.15 (dq, J=9.4, 7.0 Hz, 2H), 2.46 (m, 2H), 2.23 (m, 2H), 2.01 (m, 1H), 1.87 (m, 1H), 1.01 (t, J=7.0 Hz, 6H); $^{13}$C NMR (101 MHz, CDCl$_3$) δ 151.67 (d, J=5.9 Hz), 147.83, 146.68 (d, J=259.1 Hz), 144.35, 140.29 (d, J=9.7 Hz), 128.92, 128.18, 127.17, 107.37, 102.52, 71.05, 61.29, 35.89 (d, J=2.1 Hz), 27.21 (d, J=1.7 Hz), 18.67, 15.11; $^{19}$F NMR (376 MHz, CDCl$_3$) δ −152.93; HRMS-ESI (m/z) [M+H]$^+$ calcd for C$_{33}$H$_{35}$FN$_2$O$_2$, 510.2683. found, 510.2685.

6-(Diethoxymethyl)-3-fluoro-2-(4-fluorobenzyl)-N-tritylpyridin-4-amine

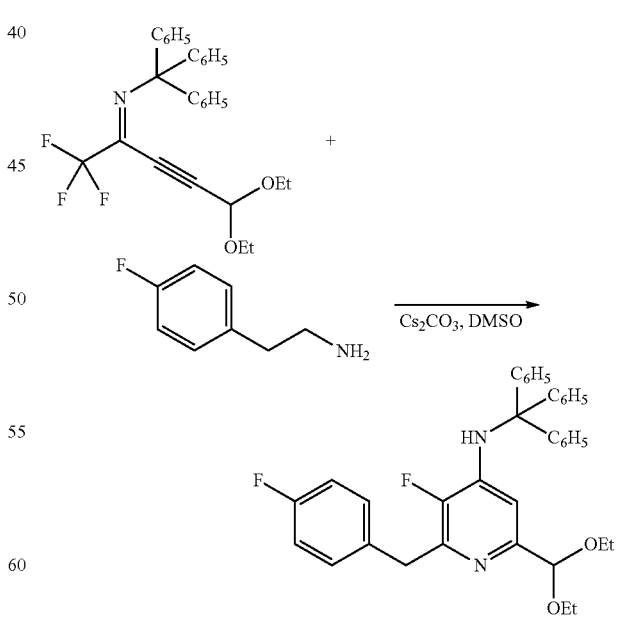

Using the procedure of Example 9, N-(5,5-diethoxy-1,1,1-trifluoropent-3-yn-2-ylidene)-1,1,1-triphenylmethanamine (4.66 g, 10 mmol), 2-(4-fluorophenyl)ethanamine (1.670 g, 12.00 mmol), cesium carbonate (8.15 g, 25.00 mmol) and DMSO (30 mL) gave 6-(diethoxymethyl)-3-fluoro-2-(4-fluorobenzyl)-N-tritylpyridin-4-amine (3.25 g, 56.4%) as a yellow glass, which crystallized from CH$_3$CN (25 mL): mp 129-130° C.; $^1$H NMR (400 MHz, CDCl$_3$) δ 7.27 (m, 19H), 6.94 (m, 2H), 6.19 (d, J=6.6 Hz, 1H), 5.71 (d, J=4.3 Hz, 1H), 5.06 (s, 1H), 4.05 (d, J=2.9 Hz, 2H), 3.23 (dq, J=9.4, 7.1 Hz, 2H), 3.13 (dq, J=9.4, 7.0 Hz, 2H), 1.00 (t, J=7.0 Hz, 6H); $^{13}$C NMR (101 MHz, CDCl$_3$) δ 161.48 (d, J=243.8 Hz), 152.10 (d, J=5.9 Hz), 147.04 (d, J=246.0 Hz), 144.65 (d, J=13.9 Hz), 144.13, 140.88 (d, J=9.4 Hz), 134.69 (d, J=3.1 Hz), 130.28 (d, J=7.8 Hz), 128.86, 128.20, 127.24, 114.99 (d, J=21.2 Hz), 108.23, 101.87, 71.24, 61.05, 37.45, 15.05; $^{19}$F NMR (376 MHz, CDCl$_3$) δ−117.27, −151.26 (dd, J=6.6, 3.6 Hz); HRMS-ESI (m/z) [M+H]$^+$ calcd for C$_{36}$H$_{34}$F$_2$N$_2$O$_2$, 564.2588. found, 564.2595.

6-(Diethoxymethyl)-3-fluoro-6'-(trifluoromethyl)-N-trityl-[2,3'-bipyridin]-4-amine

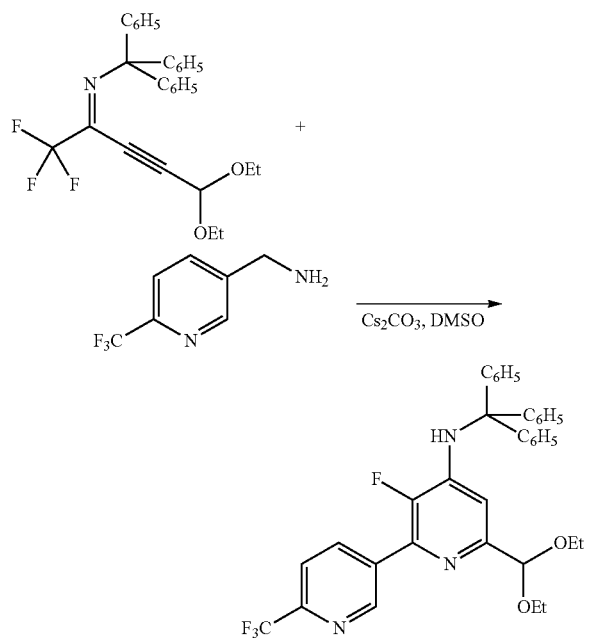

Using the procedure of Example 9, N-(5,5-diethoxy-1,1,1-trifluoropent-3-yn-2-ylidene)-1,1,1-triphenylmethanamine (2.328 g, 5 mmol), (6-(trifluoromethyl)pyridin-3-yl)methanamine (1.057 g, 6.00 mmol), cesium carbonate (4.07 g, 12.50 mmol) and DMSO (20 mL) gave 3.1 g of a dark orange oil. Column chromatography on silica gel eluting with 10% EtOAc/hexane gave 6-(diethoxymethyl)-3-fluoro-6'-(trifluoromethyl)-N-trityl-[2,3'-bipyridin]-4-amine (1.45 g, 47.2%) as an off-white solid: mp 58-60° C.; $^1$H NMR (400 MHz, CDCl$_3$) δ 9.27 (s, 1H), 8.44 (d, J=8.3 Hz, 1H), 7.76 (d, J=8.2 Hz, 1H), 7.33 (m, 15H), 6.35 (d, J=6.4 Hz, 1H), 5.96 (d, J=4.6 Hz, 1H), 5.11 (s, 1H), 3.32 (dq, J=9.4, 7.0 Hz, 2H), 3.20 (dq, J=9.4, 7.0 Hz, 2H), 1.04 (t, J=7.0 Hz, 6H); $^{13}$C NMR (101 MHz, CDCl$_3$) δ 153.41 (d, J=5.5 Hz), 150.04 (d, J=9.2 Hz), 147.52 (d, J=250.3 Hz), 147.51 (d, J=34.0 Hz), 143.82, 141.93 (d, J=9.7 Hz), 137.90, 137.49 (d, J=4.9 Hz), 134.54, 128.85, 128.38, 127.45, 120.03 (d, J=2.7 Hz), 109.35, 102.10, 71.40, 61.53, 15.06; $^{19}$F NMR (376 MHz, CDCl$_3$) δ−67.86, −149.56; HRMS-ESI (m/z) [M+H]$^+$ calcd for C$_{35}$H$_{31}$F$_4$N$_3$O$_2$, 601.2351. found, 601.2355.

6-(Diethoxymethyl)-3-fluoro-2-(thiazol-2-ylmethyl)-N-tritylpyridin-4-amine

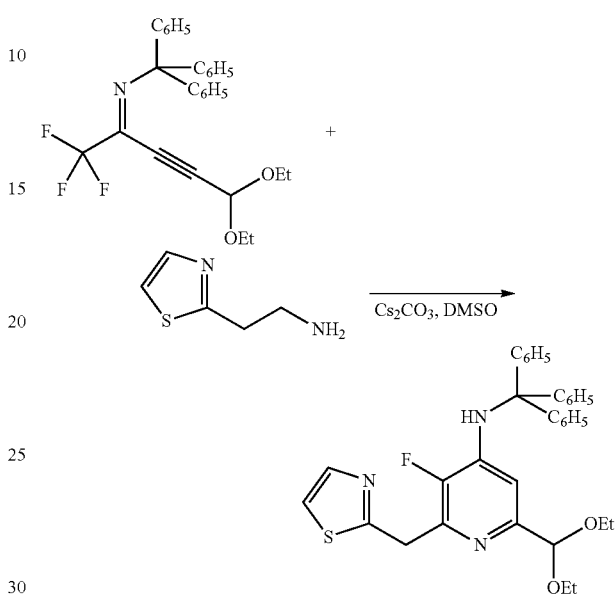

Using the procedure for Example 9, N-(5,5-diethoxy-1,1,1-trifluoropent-3-yn-2-ylidene)-1,1,1-triphenylmethanamine (2560 mg, 5.5 mmol), 2-(thiazol-2-yl)ethanamine hydrochloride (996 mg, 6.05 mmol), cesium carbonate (7168 mg, 22.00 mmol) and DMSO (30 mL) gave 2.35 g of a dark orange gum. Column chromatography on silica gel eluting with an EtOAc/hexane gradient gave 6-(diethoxymethyl)-3-fluoro-2-(thiazol-2-ylmethyl)-N-tritylpyridin-4-amine (521.5 mg, 16.61%) as a yellow glass: $^1$H NMR (400 MHz, CDCl$_3$) δ 7.70 (d, J=3.3 Hz, 1H), 7.28 (m, 15H), 7.21 (d, J=3.3 Hz, 1H), 6.23 (d, J=6.6 Hz, 1H), 5.79 (d, J=4.2 Hz, 1H), 5.08 (s, 1H), 4.51 (d, J=2.8 Hz, 2H), 3.25 (dq, J=9.4, 7.1 Hz, 2H), 3.14 (dq, J=9.4, 7.0 Hz, 2H), 1.01 (t, J=7.0 Hz, 6H); $^{13}$C NMR (101 MHz, CDCl$_3$) δ 167.44, 152.47 (d, J=5.8 Hz), 147.01 (d, J=247.7 Hz), 144.03, 142.06, 141.43 (d, J=14.0 Hz), 141.10 (d, J=9.3 Hz), 128.86, 128.24, 127.29, 119.17, 108.62, 101.75, 71.29, 61.13, 35.75, 15.05; $^{19}$F NMR (376 MHz, CDCl$_3$) δ−150.49; HRMS-ESI (m/z) [M+H]$^+$ calcd for C$_{33}$H$_{32}$FN$_3$O$_2$S, 553.2199. found, 553.2206.

6-(Diethoxymethyl)-3-fluoro-2-(tetrahydrofuran-2-yl)-N-tritylpyridin-4-amine

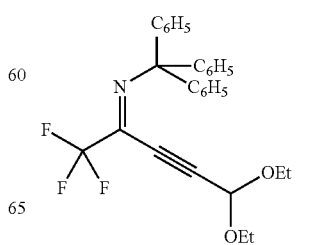

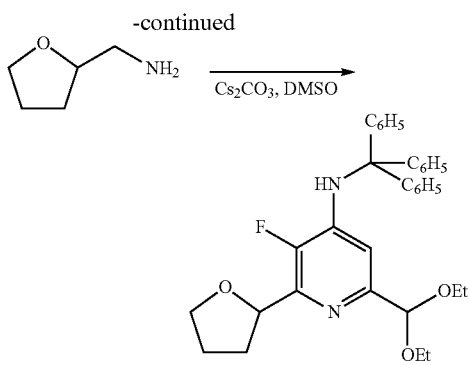

Using the procedure for Example 8, N-(5,5-diethoxy-1,1,1-trifluoropent-3-yn-2-ylidene)-1,1,1-triphenylmethanamine (4.66 g, 10 mmol), (tetrahydrofuran-2-yl)methanamine (3.03 g, 30.0 mmol), cesium carbonate (8.15 g, 25.00 mmol) and DMSO (30 mL) gave 5.2 g of a tan solid. Column chromatography on silica gel eluting with 20% EtOAc/hexane gave 6-(diethoxymethyl)-3-fluoro-2-(tetrahydrofuran-2-yl)-N-tritylpyridin-4-amine (4.48 g, 84%) as a white solid: mp 149-150° C.; $^1$H NMR (400 MHz, CDCl$_3$) δ 7.27 (m, 15H), 6.21 (d, J=6.6 Hz, 1H), 5.78 (d, J=4.5 Hz, 1H), 5.13 (t, J=7.0 Hz, 1H), 5.05 (s, 1H), 4.07 (m, 1H), 3.91 (td, J=7.8, 5.5 Hz, 1H), 3.25 (dq, J=9.4, 7.0 Hz, 2H), 3.12 (m, 2H), 2.21 (m, 3H), 1.99 (m, 1H), 1.00 (dt, J=8.7, 7.0 Hz, 6H); $^{13}$C NMR (101 MHz, CDCl$_3$) δ 151.98 (d, J=5.8 Hz), 148.35, 145.88, 145.01 (d, J=10.9 Hz), 141.01 (d, J=9.3 Hz), 128.86, 128.22, 127.22, 108.55, 102.25, 71.08, 69.01, 61.28 (d, J=22.5 Hz), 30.49, 26.48, 15.06 (d, J=2.0 Hz); $^{19}$F NMR (376 MHz, CDCl$_3$) δ −149.56 (m); HRMS-ESI (m/z) [M+H]$^+$ calcd for C$_{33}$H$_{35}$FN$_2$O$_2$, 526.2632. found, 526.2619.

2-(Diethoxymethyl)-5-fluoro-N-tritylpyridin-4-amine

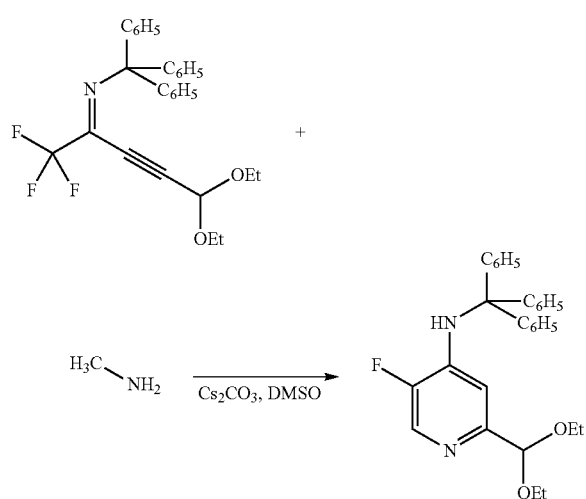

Using the procedure for Example 8, N-(5,5-diethoxy-1,1,1-trifluoropent-3-yn-2-ylidene)-1,1,1-triphenylmethanamine (4.66 g, 10 mmol, methylamine (33 weight percent (wt %) in ethanol; 4.98 mL, 40.0 mmol), cesium carbonate (8.15 g, 25.00 mmol) and DMSO (30 mL) gave 4.43 g of a dark orange oil. Column chromatography on silica gel eluting with 20% EtOAc/hexane gave 2-(diethoxymethyl)-5-fluoro-N-tritylpyridin-4-amine (2.85 g, 61.2%) as an off-white solid: mp 125-127° C.; $^1$H NMR (400 MHz, CDCl$_3$) δ 8.13 (d, J=3.1 Hz, 1H), 7.28 (m, 15H), 6.27 (d, J=7.4 Hz, 1H), 5.76 (d, J=4.0 Hz, 1H), 5.06 (s, 1H), 3.26 (dq, J=9.4, 7.1 Hz, 2H), 3.17 (dq, J=9.4, 7.0 Hz, 2H), 1.02 (t, J=7.0 Hz, 6H); $^{13}$C NMR (101 MHz, CDCl$_3$) δ 153.19 (d, J=4.3 Hz), 149.13 (d, J=246.2 Hz), 143.98, 140.96 (d, J=8.8 Hz), 134.27 (d, J=21.8 Hz), 128.84, 128.27, 127.32, 109.03, 101.77, 71.20, 61.21, 15.04; $^{19}$F NMR (376 MHz, CDCl$_3$) δ −152.74; HRMS-ESI (m/z) [M+H]$^+$ calcd for C$_{29}$H$_{29}$FN$_2$O$_2$, 456.2213. found, 456.2217.

Example 10

4-Amino-6-(4-chloro-2-fluoro-3-methoxyphenyl)-5-fluoropyridine-2-carbaldehyde

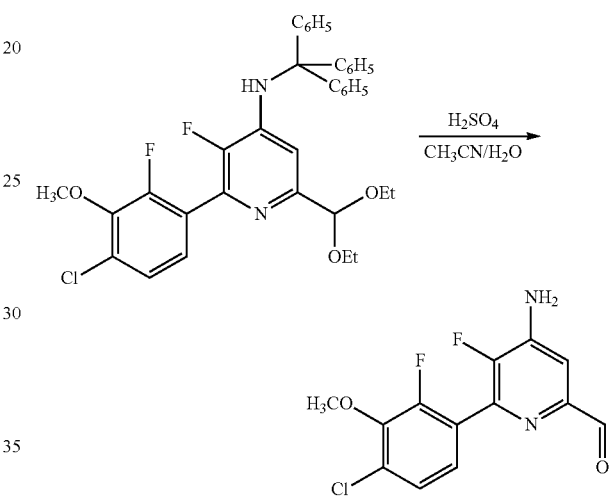

A mixture of 2-(4-chloro-2-fluoro-3-methoxyphenyl)-6-(diethoxymethyl)-3-fluoro-N-tritylpyridin-4-amine (2.117 g, 3.44 mmol), CH$_3$CN (15 mL), water (15 mL) and 1 normal (N)H$_2$SO$_4$ (7.5 mL) was placed in an oil bath and heated to 80° C. After 2 h at 80° C., an aliquot of the reaction mixture was partitioned between EtOAc and 10% sodium bicarbonate (NaHCO$_3$) and analyzed by high-performance liquid chromatography (HPLC) and TLC (80/20 hexanes/EtOAc). TLC and HPLC analyses showed only a trace of the starting material remaining (~2% by HPLC) and essentially one, more polar product.

The reaction mixture was allowed to cool to room temperature. The precipitate was removed by vacuum filtration, washing with 2:2:1 CH$_3$CN/H$_2$O/1 NH$_2$SO$_4$. HPLC analysis of this white solid showed it to be triphenylmethanol and none of the desired product. The filtrate was transferred to a separatory funnel, diluted with EtOAc (150 mL) and treated with 10% NaHCO$_3$. A white precipitate formed in the aqueous layer that did not readily extract into the organic phase. The layers were separated, and the aqueous phase was extracted with EtOAc (3×50 mL), CH$_2$Cl$_2$ (1×50 mL) and EtOAc (1×50 mL). This compound has surprisingly low solubility in both EtOAc and CH$_2$Cl$_2$. The combined organic extracts were washed with saturated NaCl (1×50 mL), dried (Na$_2$SO$_4$), filtered and concentrated in vacuo to give 1.04 g of a light tan solid. The solid was stirred with hexanes (20 mL). After stirring for 2 h, the solid was removed by vacuum filtration and washed with hexanes. The solid was air-dried for several hours to give the title compound (0.941 g, 92%) as a light tan solid: mp 191-193° C.; $^1$H NMR (400 MHz, DMSO-$d_6$) δ 9.79 (s, 1H), 7.49 (dd, J=8.5, 1.5 Hz, 1H), 7.39-7.33 (m, 2H), 6.84 (s, 2H), 3.94 (d, J=0.8 Hz, 3H); $^{19}$F NMR (376 MHz, DMSO-$d_6$) δ−129.20 (d, J=27.4 Hz), −139.73 (d, J=27.3 Hz); HRMS-ESI (m/z) [M+H]$^+$ calcd for $C_{13}H_9ClF_2N_2O_2$, 298.0321. found, 298.0322.

Example 11

4-Amino-6-(4-chlorophenyl)-5-fluoropyridine-2-carbaldehyde

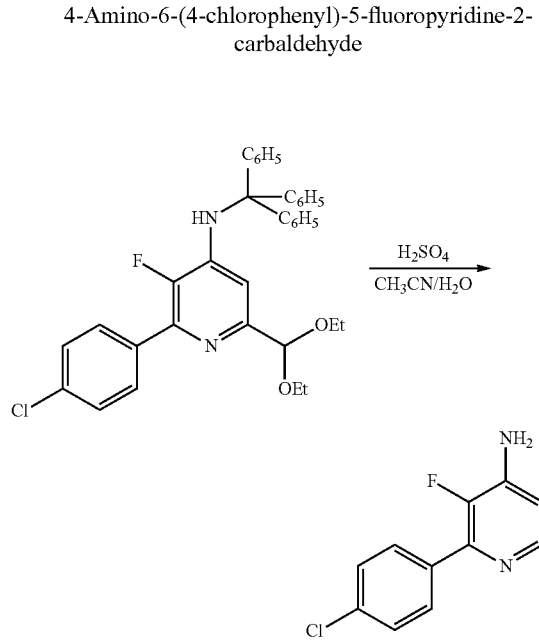

A mixture of the 2-(4-chlorophenyl)-6-(diethoxymethyl)-3-fluoro-N-tritylpyridin-4-amine (723 mg, 1.28 mmol), CH$_3$CN (5 mL), water (5 mL) and 1 NH$_2$SO$_4$ (2.5 mL) was placed in an oil bath and heated to 78° C. After 2 h at 78° C., an aliquot of the reaction mixture was partitioned between EtOAc and 10% NaHCO$_3$ and analyzed by HPLC and TLC (80/20 hexanes/EtOAc). Both TLC and HPLC analyses showed that all of the starting material had been consumed and essentially one more polar product was formed.

The reaction mixture was allowed to cool to room temperature (white precipitate present), diluted with EtOAc (75 mL) and washed with 10% NaHCO$_3$ (1×25 mL, precipitate formed in aqueous phase and was extracted into organic) and saturated NaCl (1×25 mL). The organic phase was dried (Na$_2$SO$_4$), filtered and concentrated in vacuo to give 0.65 g of a white solid. The crude material was dissolved in CH$_2$Cl$_2$/EtOAc and treated with 1.5 g of Celite. The solvent was removed in vacuo, and the residue was placed in a solid load cartridge and purified by chromatography using the following setup: Teledyne-Isco CombiFlash Companion, 40 g RediSep silica gel column, flow=40 mL/min, detection at 254 nm, solvent A=hexanes, solvent B=EtOAc. A linear gradient was used starting at 100% A (1 min) and going to 60% B over a period of 15 min Fractions containing the desired product were combined and concentrated in vacuo. The title compound (287 mg, 90%) was isolated as a fluffy, white solid: mp 173-176° C.; $^1$H NMR (400 MHz, CDCl$_3$) δ 9.95 (s, 1H), 7.96 (dd, J=8.5, 1.4 Hz, 2H), 7.48 (d, J=8.6 Hz, 2H), 7.33 (d, J=6.4 Hz, 1H), 4.55 (s, 2H); $^{19}$F NMR (376 MHz, CDCl$_3$) δ −142.53 (s); HRMS-ESI (m/z) [M+H]$^+$ calcd for $C_{12}H_8ClFN_2O$, 250.0309. found, 250.0315.

Example 12

4-Amino-5-fluoro-6-propylpicolinaldehyde

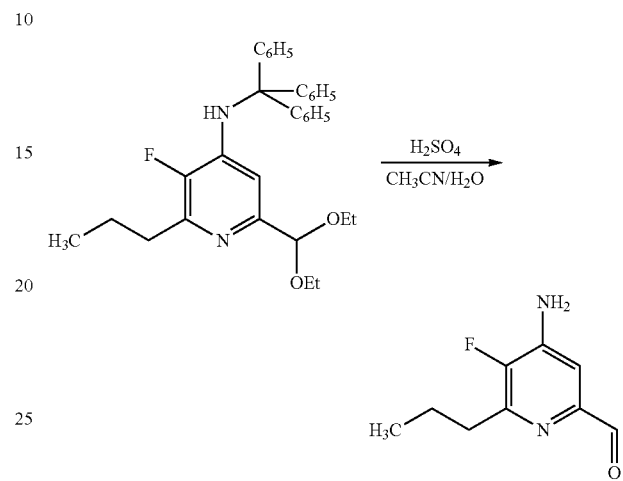

A magnetically stirred mixture of 6-(diethoxymethyl)-3-fluoro-2-propyl-N-tritylpyridin-4-amine (3.74 g, 7.50 mmol), concentrated (conc) H$_2$SO$_4$ (1.5 mL), CH$_3$CN (35 mL) and water (35 mL) was heated to reflux for 2 h. Upon cooling to room temperature, the mixture was added to CH$_2$Cl$_2$ (100 mL) and H$_2$O (50 mL). The aqueous layer was washed with additional CH$_2$Cl$_2$ (50 mL). The aqueous layer was made basic with a saturated solution of sodium carbonate (Na$_2$CO$_3$) and was washed with CH$_2$Cl$_2$ (2×50 mL). The combined organic layers were washed with H$_2$O (50 mL), a saturated solution of NaCl (50 mL) and dried (MgSO$_4$). Solvent removal gave 4-amino-5-fluoro-6-propylpicolinaldehyde (1.21 g, 84%) as a white solid: mp 113-114° C.; $^1$H NMR (400 MHz, CDCl$_3$) δ 9.88 (s, 1H), 7.23 (d, J=6.7 Hz, 1H), 4.42 (br s, 2H), 2.82 (m, 3H), 1.77 (m, 2H), 1.00 (t, J=7.4 Hz, 3H): $^{13}$C NMR (101 MHz, CDCl$_3$) δ 193.06, 150.03 (d, J=25.6 Hz), 148.71 (d, J=5.5 Hz), 148.70 (d, J=213.1 Hz), 141.32 (d, J=12.6 Hz), 107.56 (d, J=3.7 Hz), 33.32 (d, J=1.4 Hz), 21.85 (d, J=1.2 Hz), 13.90; $^{19}$F NMR (376 MHz CDCl$_3$) δ −144.42 (m); HRMS-ESI (m/z) [M+H]$^+$ calcd for $C_9H_{12}ClFN_2O$, 182.0855. found, 182.0854.

4-Amino-6-(tert-butyl)-5-fluoropicolinaldehyde

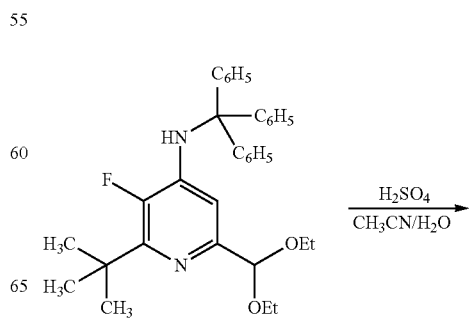

-continued

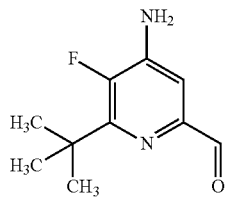

Using the procedure for Example 12, 2-(tert-butyl)-6-(diethoxymethyl)-3-fluoro-N-tritylpyridin-4-amine (2461 mg, 4.8 mmol), conc $H_2SO_4$ (1 mL), $CH_3CN$ (35 mL) and $H_2O$ (35 mL) gave 4-amino-6-(tert-butyl)-5-fluoropicolinaldehyde (718 mg, 73.2%) as a white solid: mp 129-130° C.; $^1$H NMR (400 MHz, $CDCl_3$) δ 9.86 (s, 1H), 7.26 (d, J=6.3 Hz, 2H), 4.37 (s, 2H), 1.43 (d, J=1.5 Hz, 9H); $^{13}$C NMR (101 MHz, $CDCl_3$) δ 193.06, 149.83 (d, J=14.8 Hz), 148.90 (d, J=253.5 Hz), 148.71 (d, J=5.5 Hz), 141.32 (d, J=12.6 Hz), 107.56 (d, J=3.7 Hz), 33.32 (d, J=1.4 Hz), 21.85 (d, J=1.2 Hz), 13.90; $^{19}$F NMR (376 MHz, $CDCl_3$) δ −137.45 (d, J=4.6 Hz); HRMS-ESI (m/z) [M+H]$^+$ calcd for $C_{10}H_{13}FN_2O$, 196.1012. found, 196.0994.

4-Amino-6-(cyclopropylmethyl)-5-fluoropicolinaldehyde

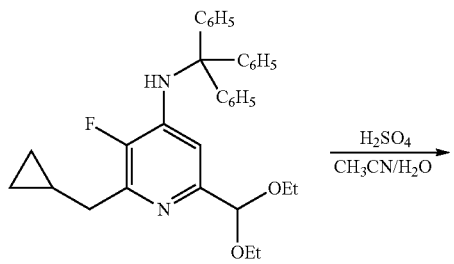

Using the procedure for Example 12, 2-(cyclopropylmethyl)-6-(diethoxymethyl)-3-fluoro-N-tritylpyridin-4-amine (4.34 g, 8.5 mmol), conc $H_2SO_4$ (1 mL), $CH_3CN$ (35 mL) and $H_2O$ (35 mL) gave 4-amino-6-(cyclopropylmethyl)-5-fluoropicolinaldehyde (1.48 g, 88%) as an off-white solid: mp 99-100° C.; $^1$H NMR (400 MHz, $CDCl_3$) δ 9.89 (s, 1H), 7.25 (d, J=6.7 Hz, 1H), 4.40 (br s, 2H), 2.76 (dd, J=7.0, 2.9 Hz, 2H), 1.17 (m, 1H), 0.50 (m, 2H), 0.29 (m, 2H); $^{13}$C NMR (101 MHz, $CDCl_3$) δ 193.10, 149.43 (d, J=15.4 Hz), 148.84 (d, J=253.6 Hz), 148.73 (d, J=5.4 Hz), 141.49 (d, J=12.6 Hz), 107.76 (d, J=3.8 Hz), 36.25 (d, J=1.8 Hz), 10.16 (d, J=1.5 Hz), 4.56; $^{19}$F NMR (376 MHz $CDCl_3$) δ −144.19. HRMS-ESI (m/z) [M+H]$^+$ calcd for $C_{10}H_{11}FN_2O$, 194.0855. found, 194.0857.

4-Amino-6-cyclobutyl-5-fluoropicolinaldehyde

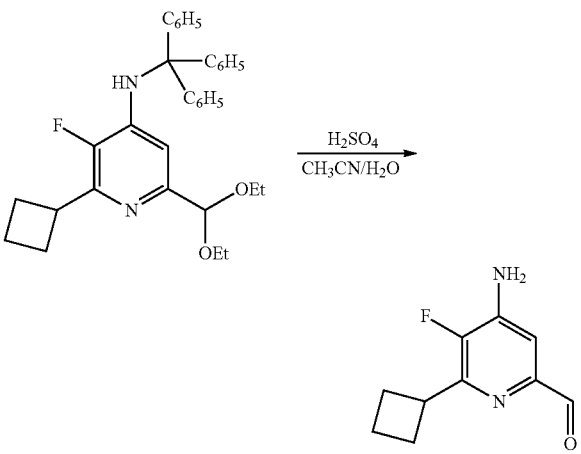

Using the Procedure of Example 12, 2-cyclobutyl-6-(diethoxymethyl)-3-fluoro-N-tritylpyridin-4-amine (2.298 g, 4.5 mmol), conc $H_2SO_4$ (1 mL), $CH_3CN$ (35 mL) and $H_2O$ (35 mL) gave 4-amino-6-cyclobutyl-5-fluoropicolinaldehyde (0.780 g, 88%) as a white solid: mp 134-135° C.; $^1$H NMR (400 MHz, $CDCl_3$) δ 9.92 (s, 1H), 7.22 (d, J=6.7 Hz, 1H), 4.34 (s, 2H), 3.90 (m, 2H), 2.51 (pd, J=9.3, 2.4 Hz, 3H), 2.32 (qt, J=8.5, 2.7 Hz, 3H), 2.03 (m, 4H); $^{13}$C NMR (101 MHz, $CDCl_3$) δ 193.39, 151.45 (d, J=14.5 Hz), 148.62 (d, J=5.4 Hz), 148.24 (d, J=253.9 Hz), 141.03 (d, J=12.5 Hz), 107.43 (d, J=3.6 Hz), 35.38 (d, J=2.0 Hz), 27.00 (d, J=1.6 Hz), 18.64; $^{19}$F NMR (376 MHz, $CDCl_3$) δ −144.82; HRMS-ESI (m/z) [M+H]$^+$ calcd for $C_{10}H_{11}FN_2O$, 194.0855. found, 194.0855.

4-Amino-5-fluoro-6-(4-fluorobenzyl)picolinaldehyde

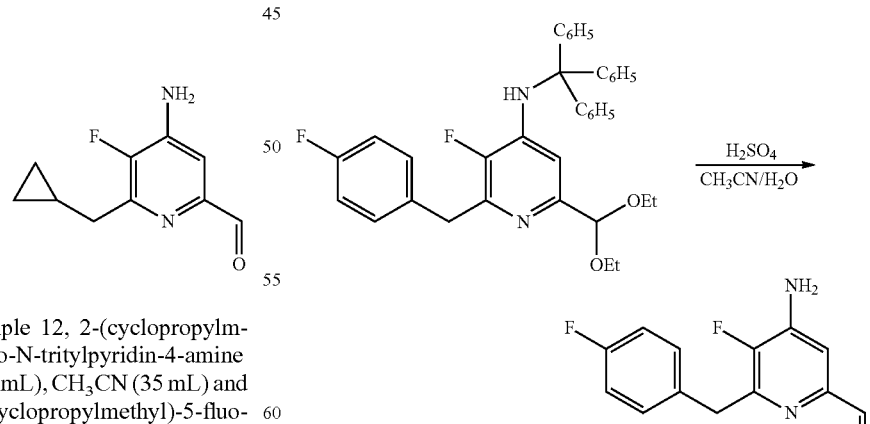

Using the procedure for Example 12, 6-(diethoxymethyl)-3-fluoro-2-(4-fluorobenzyl)-N-tritylpyridin-4-amine (2.82 g, 5 mmol), conc $H_2SO_4$ (1 mL), $CH_3CN$ (35 mL) and $H_2O$ (35 mL) gave 4-amino-5-fluoro-6-(4-fluorobenzyl)picolinaldehyde (1.05 g, 83%) as a white solid: mp 130-131° C.; ¹H NMR (400 MHz, CDCl₃) δ 9.87 (s, 1H), 7.29 (m, 2H), 7.25 (d, J=6.7 Hz, 1H), 6.97 (m, 2H), 4.45 (s, 2H), 4.14 (d, J=3.1 Hz, 2H); ¹³C NMR (101 MHz, CDCl₃) δ 192.85, 161.67 (d, J=244.6 Hz), 148.87 (d, J=5.4 Hz), 148.70 (d, J=254.7 Hz), 148.03 (d, J=13.7 Hz), 141.77 (d, J=12.3 Hz), 133.71 (d, J=2.7 Hz), 130.32 (d, J=8.1 Hz), 115.30 (d, J=21.3 Hz), 108.09 (d, J=3.9 Hz), 37.09; ¹⁹F NMR (376 MHz, CDCl₃) δ −116.54 (m), −143.54 (dt, J=6.1, 2.7 Hz); HRMS-ESI (m/z) [M+H]⁺ calcd for $C_{13}H_{10}F_2N_2O$, 248.0761. found, 248.0763.

4-Amino-3-fluoro-6'-(trifluoromethyl)-[2,3'-bipyridine]-6-carbaldehyde

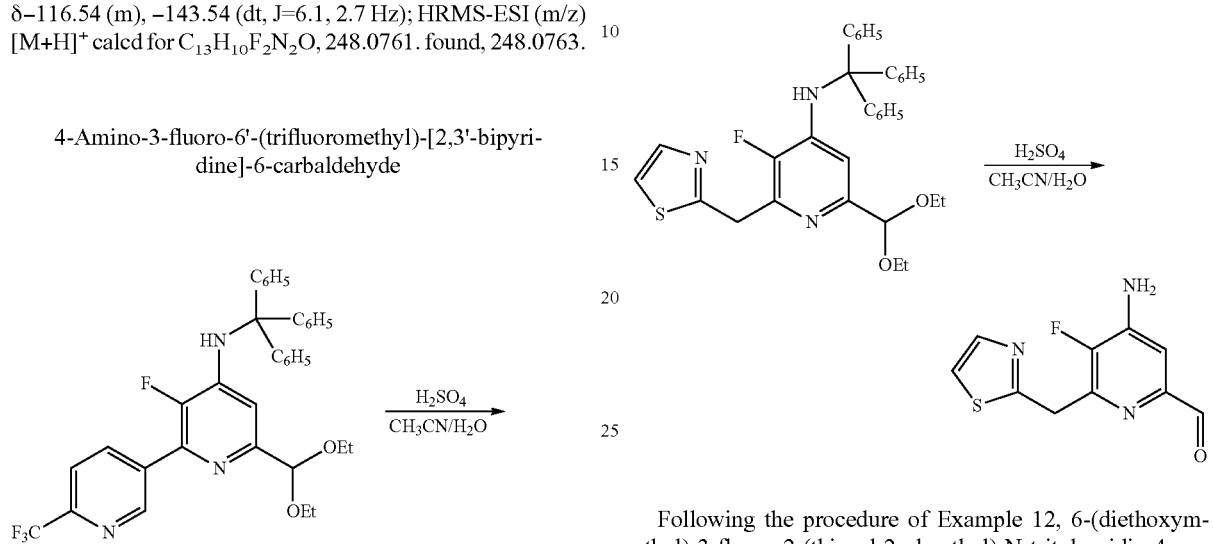

Following the procedure of Example 12, 6-(diethoxymethyl)-3-fluoro-6'-(trifluoromethyl)-N-trityl-[2,3'-bipyridin]-4-amine (1203 mg, 2 mmol), conc H₂SO₄ (0.5 mL), CH₃CN (25 mL) and H₂O (25 mL) gave 4-amino-3-fluoro-6'-(trifluoromethyl)-[2,3'-bipyridine]-6-carbaldehyde (248 mg, 0.861 mmol, 43.0%) as a white solid: mp 166-167° C.; ¹H NMR (400 MHz, CDCl₃) δ 9.97 (s, 1H), 9.35 (s, 1H), 8.54 (d, J=8.2 Hz, 1H), 7.84 (d, J=8.2 Hz, 1H), 7.40 (d, J=6.5 Hz, 1H), 4.67 (s, 2H); ¹³C NMR (101 MHz, CDCl₃) δ 192.35, 149.96 (d, J=8.9 Hz), 149.50 (d, J=5.2 Hz), 149.03 (d, J=260.1 Hz), 145.2, 143.03 (d, J=12.4 Hz), 140.95, 137.48 (d, J=5.3 Hz), 133.55, 122.83, 120.25 (d, J=2.7 Hz), 108.70 (d, J=4.3 Hz); ¹⁹F NMR (376 MHz, CDCl₃) δ −67.98, −142.26; HRMS-ESI (m/z) [M+H]⁺ calcd for $C_{12}H_7F_4N_3O$, 285.0525. found, 285.0525.

4-Amino-5-fluoro-6-(thiazol-2-ylmethyl)picolinaldehyde

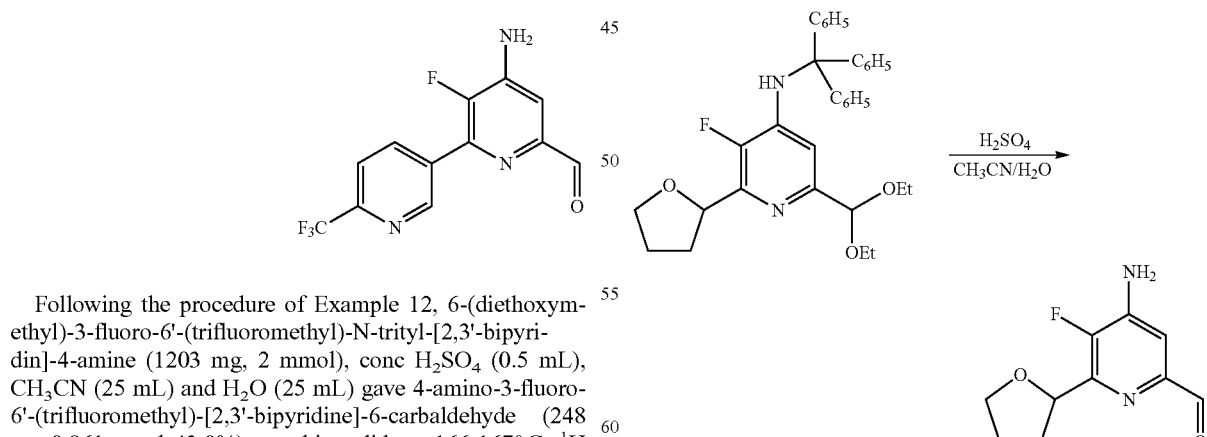

Following the procedure of Example 12, 6-(diethoxymethyl)-3-fluoro-2-(thiazol-2-ylmethyl)-N-tritylpyridin-4-amine (471 mg, 0.85 mmol), conc H₂SO₄ (0.5 mL), CH₃CN (10 mL) and H₂O (10 mL) gave the title compound (0.145 g, 71%) as an off-white solid: ¹H NMR (400 MHz, CDCl₃) δ 9.88 (s, 1H), 7.72 (d, J=3.3 Hz, 1H), 7.28 (d, J=6.7 Hz, 1H), 7.26 (d, J=3.4 Hz, 1H), 4.59 (d, J=2.8 Hz, 2H), 4.56 (br s, 2H); ¹⁹F NMR (376 MHz, DMSO-d₆) δ −142.44; HRMS-ESI (m/z) [M+H]⁺ calcd for $C_{10}H_8FN_3OS$, 237.0372. found, 237.0363.

4-Amino-5-fluoro-6-(tetrahydrofuran-2-yl)picolinaldehyde

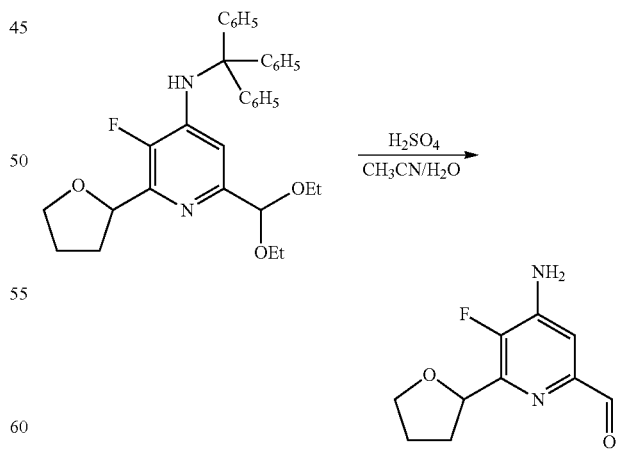

Using the procedure of Example 12, 6-(diethoxymethyl)-3-fluoro-2-(tetrahydrofuran-2-yl)-N-tritylpyridin-4-amine (4.21 g, 8 mmol), conc H₂SO₄ (1 mL), CH₃CN (35 mL) and H₂O (35 mL) gave 4-amino-5-fluoro-6-(tetrahydrofuran-2-yl)picolinaldehyde (1.61 g, 95%) as a white solid: mp 122-

123° C.; $^1$H NMR (400 MHz, CDCl$_3$) δ 9.90 (s, 1H), 7.28 (d, J=6.7 Hz, 1H), 5.26 (td, J=7.1, 1.7 Hz, 1H), 4.46 (br s, 2H), 4.17 (dt, J=7.9, 6.9 Hz, 1H), 3.98 (td, J=7.8, 5.6 Hz, 1H), 2.29 (m, 2H), 2.19 (m, 1H), 2.05 (m, 1H); $^{13}$C NMR (101 MHz, CDCl$_3$) δ 193.12, 148.75 (d, J=5.2 Hz), 148.60 (d, J=11.7 Hz), 148.53 (d, J=256.8 Hz), 142.02 (d, J=12.1 Hz), 108.33 (d, J=4.1 Hz), 75.70, 69.26, 30.78 (d, J=0.9 Hz), 26.28; $^{19}$F NMR (376 MHz, CDCl$_3$) δ −144.90 (d, J=6.6 Hz); HRMS-ESI (m/z) [M+H]$^+$ calcd for C$_{10}$H$_{11}$FN$_2$O$_2$, 210.0805. found, 210.0803.

4-Amino-5-fluoropicolinaldehyde

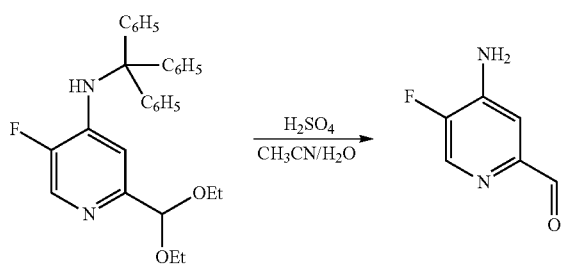

Following the procedure for Example 12, 2-(diethoxymethyl)-5-fluoro-N-tritylpyridin-4-amine (457 mg, 1 mmol), conc H$_2$SO$_4$ (0.2 mL), CH$_3$CN (5 mL) and H$_2$O (5 mL) gave 4-amino-5-fluoropicolinaldehyde (126 mg, 87%) as a white solid: mp 133-135° C.; $^1$H NMR (400 MHz, CDCl$_3$) δ 9.90 (s, 1H), 8.34 (d, J=2.7 Hz, 1H), 7.36 (d, J=7.5 Hz, 1H), 4.47 (br s, 2H); $^{19}$F NMR (376 MHz, CDCl$_3$) δ −144.44; HRMS-ESI (P/z) [M+H]$^+$ calcd for C$_6$H$_5$FN$_2$O, 140.0386. found, 140.0384.

Example 13

4-Amino-3-chloro-6-(4-chloro-2-fluoro-3-methoxyphenyl)-5-fluoropyridine-2-carbaldehyde

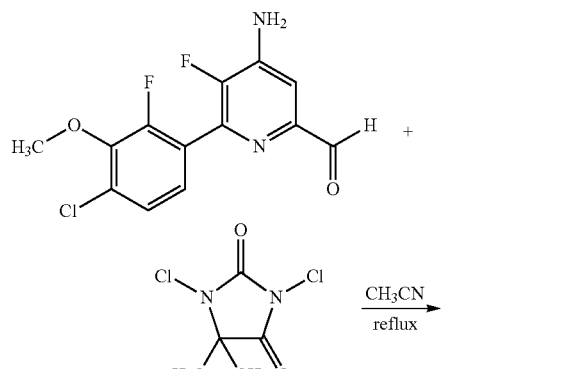

A 100 mL round bottom flask equipped with a magnetic stir bar and reflux condenser was charged with 4-amino-6-(4-chloro-2-fluoro-3-methoxyphenyl)-5-fluoropyridine-2-carbaldehyde (0.851 g, 2.85 mmol), CH$_3$CN (30 mL) and 1,3-dichloro-5,5-dimethylimidazolidine-2,4-dione (0.309 g, 1.567 mmol, 0.55 equiv). The resultant light yellow mixture was stirred at room temperature for 5 min and then heated to reflux under an atmosphere of N$_2$. After stirring at reflux for 30 min, the reaction mixture had become a yellow, homogenous solution. After stirring at reflux for 60 min, an aliquot of the reaction mixture was partitioned between EtOAc and H$_2$O and analyzed by TLC (80/20 hexanes/EtOAc) and HPLC. Both TLC and HPLC indicated that all of the starting material had been consumed and essentially one, slightly less polar product formed. The reaction mixture was allowed to cool to room temperature, diluted with EtOAc (150 mL) and washed with H$_2$O (1×50 mL), dilute sodium bisulfite (1.0 g NaHSO$_3$/50 mL H$_2$O; 1×50 mL) and saturated NaCl (1×50 mL). The organic phase was dried (Na$_2$SO$_4$), filtered and concentrated in vacuo to give 1.00 g of a tan solid.

The crude material was dissolved in acetone and treated with 3 g of Celite. The solvent was removed in vacuo, and the residue placed in a solid load cartridge and purified by chromatography using the following setup: Teledyne-Isco CombiFlash Companion, 40 g RediSep silica gel column, flow=40 mL/min, detection at 254 nm, solvent A=hexanes, solvent B=EtOAc. A linear gradient was used starting at 95% A/5% B (1 min) and going to 100% B over a period of 15 min. The desired product came off the column in 30 fractions and did not appear to give any separation. Fractions containing the desired product were combined and concentrated in vacuo to give 0.870 g of a light tan solid. $^1$H NMR still shows what appears to be contamination from 5,5-dimethylhydantoin. The impure material was stirred with a 2:1 mixture of H$_2$O/CH$_3$CN (15 mL). After stirring for 3 h, the solid was removed by vacuum filtration, washing with 1:1 H$_2$O/CH$_3$CN (10 mL). The solid was air-dried for an hour and then transferred to a 25 mL round bottom flask, treated with CH$_3$CN and concentrated in vacuo (4×5 mL). The title compound (749 mg, 79%) was isolated as a light tan solid: mp 192-196° C.; $^1$H NMR (400 MHz, DMSO-d$_6$) δ 9.97 (s, 1H), 7.51 (dd, J=8.5, 1.2 Hz, 1H), 7.41-7.31 (m, 1H), 7.15 (s, 2H), 3.94 (s, 4H); $^{19}$F NMR (376 MHz, DMSO-d$_6$) δ −129.20 (d, J=27.9 Hz), −134.34 (d, J=28.0 Hz); HRMS-ESI (m/z) [M+H]$^+$ calcd for C$_{13}$H$_8$Cl$_2$F$_2$N$_2$O$_2$, 331.9931. found, 331.9930.

Example 14

4-Amino-3-chloro-6-(4-chlorophenyl)-5-fluoropyridine-2-carbaldehyde

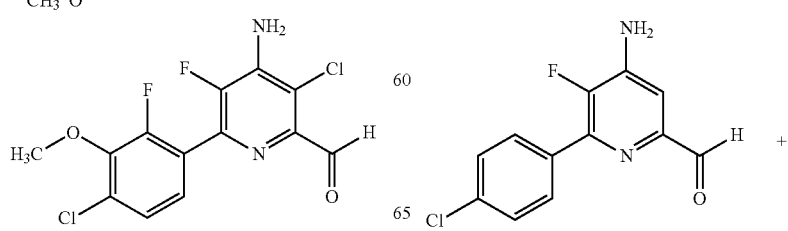

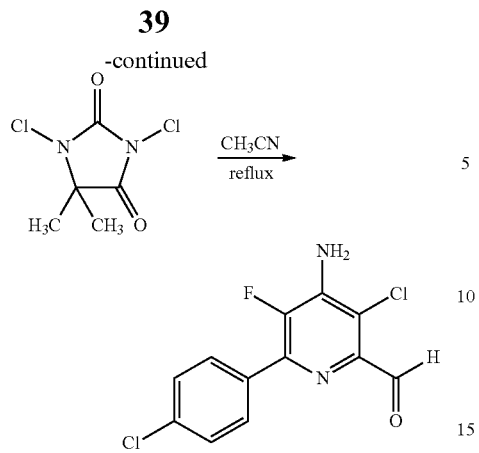

A mixture of 4-amino-6-(4-chlorophenyl)-5-fluoropyridine-2-carbaldehyde (257 mg, 1.03 mmol) in CH₃CN (10 mL; not homogenous) was treated with 1,3-dichloro-5,5-dimethylimidazolidine-2,4-dione (111 mg, 0.564 mmol) while stirring at room temperature under an atmosphere of N₂. The reaction mixture gradually turned into a yellow, homogenous solution. After stirring at room temperature for 90 min, an aliquot of the reaction mixture was partitioned between EtOAc and H₂O and analyzed by TLC (80/20 hexanes/EtOAc) and HPLC. HPLC analysis still showed starting material (SM) present (~1:1 SM/product). After an additional 30 min at room temperature, the reaction mixture was heated to reflux. Within 30 min the reaction mixture had turned green in color. After stirring at reflux for 60 min, HPLC analysis indicated that all of the starting material had been consumed.

The reaction mixture was allowed to cool to room temperature, diluted with EtOAc (75 mL) and washed with H₂O (1×25 mL), dilute sodium bisulfite (0.5 g NaHSO₃/25 mL H₂O, 1×25 mL) and saturated NaCl (1×25 mL). The organic phase was dried (Na₂SO₄), filtered and concentrated in vacuo to give 0.33 g of a green solid. The crude material was dissolved in EtOAc and treated with 1 g of Celite. The solvent was removed in vacuo, and the residue placed in a solid loading cartridge and purified by chromatography using the following setup: Teledyne-Isco CombiFlash Companion, 24 g RediSep silica gel column, flow 40=mL/min, detection at 254 nm, solvent A=hexanes, solvent B=EtOAc. A linear gradient was used starting at 100% A (1 min) and going to 70% B over a period of 10 min Fractions containing the desired product were combined and concentrated in vacuo. The title compound (232 mg, 79%) was isolated as a light tan solid: mp 166-169° C.; ¹H NMR (400 MHz, CDCl₃) δ 10.12 (s, 1H), 7.99-7.93 (m, 2H), 7.50-7.45 (m, 2H), 4.98 (s, 2H); ¹⁹F NMR (376 MHz, CDCl₃) δ −137.68 (s); ESIMS m/z 286 ([M+H]⁺), 283 ([M−H]⁻).

Example 15

4-Amino-3-chloro-5-fluoro-6-propylpicolinaldehyde

To a flask equipped with a stir bar and reflux condenser was added 4-amino-5-fluoro-6-propylpicolinaldehyde (0.250 g, 1.372 mmol) and 1,3-dichloro-5,5-dimethylimidazolidine-2,4-dione (0.149 g, 0.755 mmol). The flask was sealed, evacuated and backfilled with N₂. Acetonitrile (13.72 mL) was added, and the reaction mixture was stirred at room temperature for ~5 min, then heated to reflux (~2 h). The reaction mixture color changed from yellow to orange then green over the course of 2 h. The reaction mixture was cooled to room temperature, diluted with EtOAc and washed with H₂O. The layers were separated, and the organic layer was washed with dilute sodium bisulfite followed by saturated NaCl. The organic layer was dried (Na₂SO₄), filtered and concentrated onto silica. Purification via flash chromatography (silica; EtOAc, Hex) yielded 4-amino-3-chloro-5-fluoro-6-propylpicolinaldehyde (97 mg, 32.6%) as an off-white solid: mp 89-91° C.; ¹H NMR (400 MHz, CDCl₃) δ 10.09 (s, 1H), 4.81 (s, 2H), 2.81 (m, 2H), 1.76 (m, 2H), 0.99 (t, J=7.4 Hz, 3H); ¹⁹F NMR (376 MHz, CDCl₃) δ −139.62; ¹³C NMR (101 MHz, CDCl₃) δ 191.27, 152.80, 149.26, 146.64, 141.87, 139.82, 115.77, 37.04, 28.53.

4-Amino-6-(tert-butyl)-3-chloro-5-fluoropicolinaldehyde

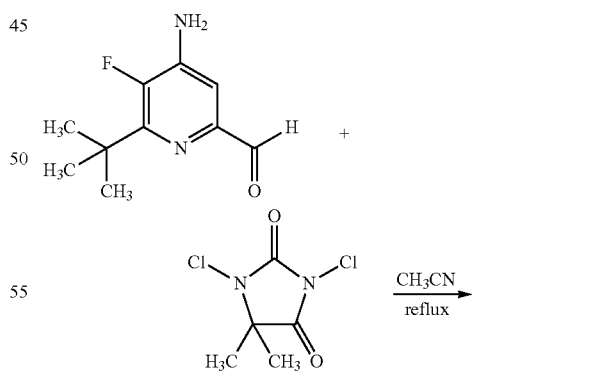

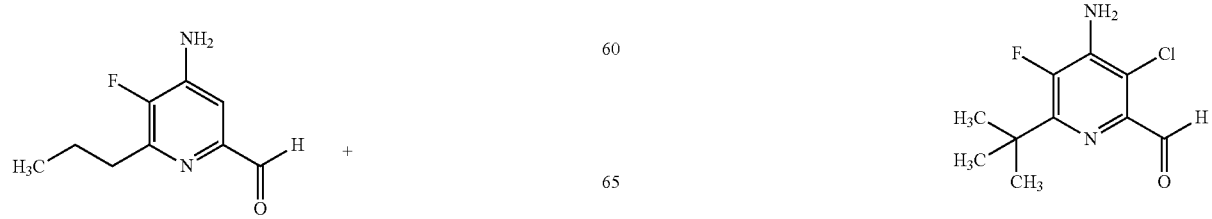

Using the procedure for Example 15, 4-amino-6-(tert-butyl)-5-fluoropicolinaldehyde (0.5 g, 2.55 mol), 1,3-dichloro-5,5-dimethylimidazolidine-2,4-dione (0.276 g, 1.401 mol) CH$_3$CN (26 mL) gave 4-amino-6-(tert-butyl)-3-chloro-5-fluoropicolinaldehyde (423 mg, 70.5%) as a yellow oil: $^1$H NMR (400 MHz, CDCl$_3$) δ 10.01 (s, 1H), 4.76 (d, J=7.2 Hz, 3H), 1.42 (d, J=1.6 Hz, 9H); $^{19}$F NMR (376 MHz, CDCl$_3$) δ −132.69; $^{13}$C NMR (101 MHz, CDCl$_3$) δ 191.27, 152.89, 149.20, 146.51, 141.75, 139.93, 36.97, 28.39; EIMS m/z 230.

4-Amino-3-chloro-6-(cyclopropylmethyl)-5-fluoropicolinaldehyde

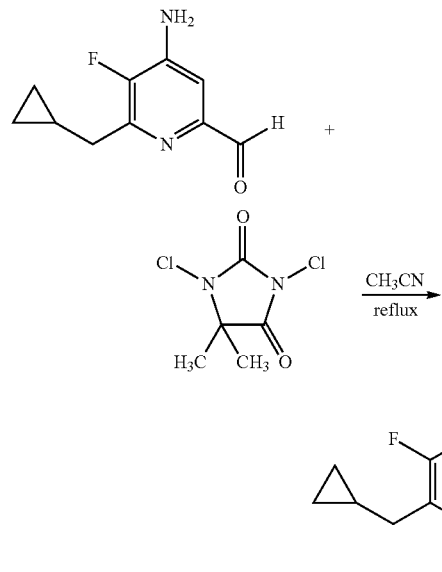

Using the procedure for Example 15, 4-amino-6-(cyclopropylmethyl)-5-fluoropicolinaldehyde (0.5 g, 2.57 mmol), 1,3-dichloro-5,5-dimethylimidazolidine-2,4-dione (0.279 g, 1.416 mmol) and CH$_3$CN (26 mL) gave 4-amino-3-chloro-6-(cyclopropylmethyl)-5-fluoropicolinaldehyde (138 mg, 0.604 mmol, 23.44%) as an orange oil: $^1$H NMR (400 MHz, CDCl$_3$) δ 10.09 (s, 1H), 4.83 (s, 3H), 2.75 (dd, J=7.0, 2.8 Hz, 3H), 1.26 (t, J=7.1 Hz, 1H), 0.50 (m, 3H), 0.28 (dt, J=6.2, 4.6 Hz, 3H); $^{19}$F NMR (376 MHz, CDCl$_3$) δ −139.49; $^{13}$C NMR (101 MHz, CDCl$_3$) δ 190.47, 148.35, 147.05, 145.79, 143.11, 139.40, 116.45, 36.23, 10.04, 4.51.

4-Amino-3-chloro-6-cyclobutyl-5-fluoropicolinaldehyde

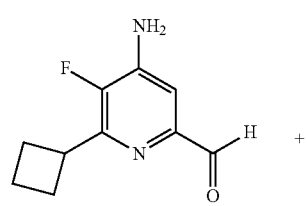

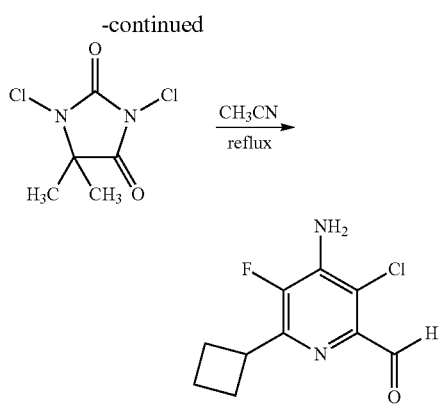

Using the procedure for Example 15, 4-amino-6-cyclobutyl-5-fluoropicolinaldehyde (0.5 g, 2.57 mol), 1,3-dichloro-5,5-dimethylimidazolidine-2,4-dione (0.279 g, 1.416 mol) and CH$_3$CN (26 mL) gave 4-amino-3-chloro-6-cyclobutyl-5-fluoropicolinaldehyde (289 mg, 45.7%) as a red foam: $^1$H NMR (400 MHz, CDCl$_3$) δ 10.09 (s, 1H), 4.77 (d, J=9.4 Hz, 2H), 3.87 (ttdd, J=9.3, 8.3, 2.3, 1.1 Hz, 2H), 2.49 (m, 2H), 2.30 (m, 2H), 2.10 (m, 1H), 1.95 (tddd, J=13.4, 7.1, 3.5, 2.1 Hz, 1H); $^{19}$F NMR (376 MHz, CDCl$_3$) δ −140.24; $^{13}$C NMR (101 MHz, CDCl$_3$) δ 191.04, 149.06, 147.71, 145.14, 142.84, 139.20, 115.84, 35.24, 26.86, 18.62; EIMS m/z 228.

4-Amino-3-chloro-5-fluoro-6-(4-fluorobenzyl)picolinaldehyde

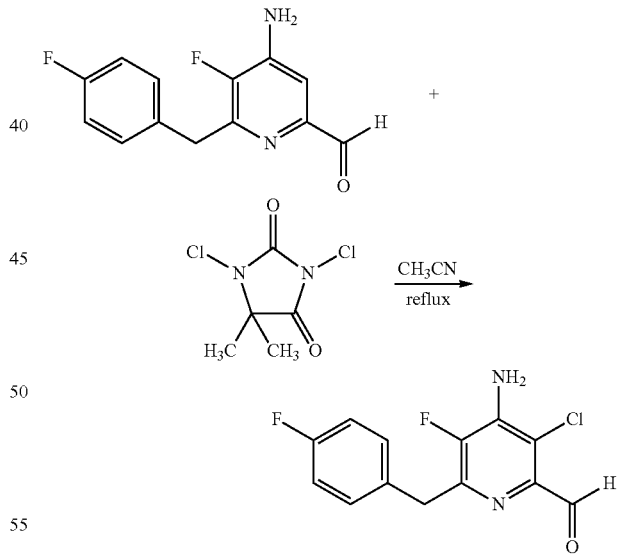

Using the procedure for Example 15, 4-amino-5-fluoro-6-(4-fluorobenzyl)-picolinaldehyde (0.5 g, 2.014 mmol), 1,3-dichloro-5,5-dimethylimidazolidine-2,4-dione (0.218 g, 1.108 mmol) and CH$_3$CN (20 mL) gave 4-amino-3-chloro-5-fluoro-6-(4-fluorobenzyl)picolinaldehyde (428 mg, 73.7%) as an orange solid: mp 109-111° C.; $^1$H NMR (400 MHz, CDCl$_3$) δ 10.08 (s, 1H), 7.28 (m, 3H), 6.97 (m, 2H), 4.84 (s, 2H), 4.14 (d, J=3.1 Hz, 2H); $^{19}$F NMR (376 MHz, CDCl$_3$) δ −116.40, −139.04; $^{13}$C NMR (101 MHz, CDCl$_3$) δ 190.27, 162.96, 160.53, 148.18, 145.80, 145.67, 145.61, 143.17, 139.85, 139.72, 133.24, 130.38, 130.31, 115.47, 115.26, 37.10, 37.08; EIMS m/z 282.

4-Amino-5-chloro-3-fluoro-6'-(trifluoromethyl)-[2,3'-bipyridine]-6-carbaldehyde

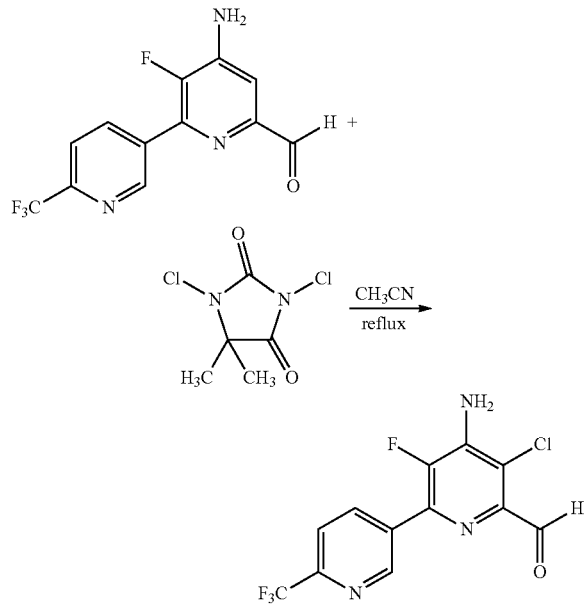

Using the procedure for Example 15, 4-amino-3-fluoro-6'-(trifluoromethyl)-[2,3'-bipyridine]-6-carbaldehyde (200 mg, 0.701 mmol), 1,3-dichloro-5,5-dimethylimidazolidine-2,4-dione (76 mg, 0.386 mmol) and CH$_3$CN (7 mL) gave 4-amino-5-chloro-3-fluoro-6'-(trifluoromethyl)-[2,3'-bipyridine]-6-carbaldehyde (182 mg, 69.8%) as a yellow solid: mp 147-149° C.; $^1$H NMR (400 MHz, CDCl$_3$) δ 10.14 (s, 1H), 9.34 (d, J=2.0 Hz, 1H), 8.54 (m, 1H), 7.84 (m, 1H), 5.13 (s, 2H); $^{19}$F NMR (376 MHz, CDCl$_3$) δ −68.02, −137.62.

4-Amino-3-chloro-5-fluoro-6-(tetrahydrofuran-2-yl)picolinaldehyde

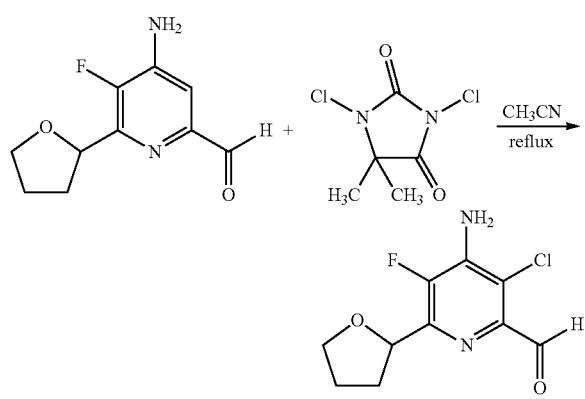

Using the procedure for Example 15, 4-amino-5-fluoro-6-(tetrahydrofuran-2-yl)picolinaldehyde (0.5 g, 2.379 mmol), 1,3-dichloro-5,5-dimethylimidazolidine-2,4-dione (0.258 g, 1.308 mmol) and CH$_3$CN (24 mL) gave 4-amino-3-chloro-5-fluoro-6-(tetrahydrofuran-2-yl)picolinaldehyde (59 mg, 10.14%) as a yellow oil: $^1$H NMR (400 MHz, CDCl$_3$) δ 10.04 (m, 1H), 5.24 (td, J=7.0, 1.7 Hz, 1H), 4.86 (d, J=9.6 Hz, 2H), 4.11 (m, 1H), 3.98 (td, J=7.8, 5.6 Hz, 1H), 2.30 (m, 2H), 1.26 (m, 2H); $^{19}$F NMR (376 MHz, CDCl$_3$) δ −140.28; $^{13}$C NMR (101 MHz, CDCl$_3$) δ 190.69, 148.31, 146.23, 145.56, 143.05, 139.88, 75.77, 69.34, 30.51, 26.31; EIMS m/z 243.

Example 16

4-Amino-3-chloro-6-(4-chloro-2-fluoro-3-methoxyphenyl)-5-fluoropyridine-2-carboxylic acid

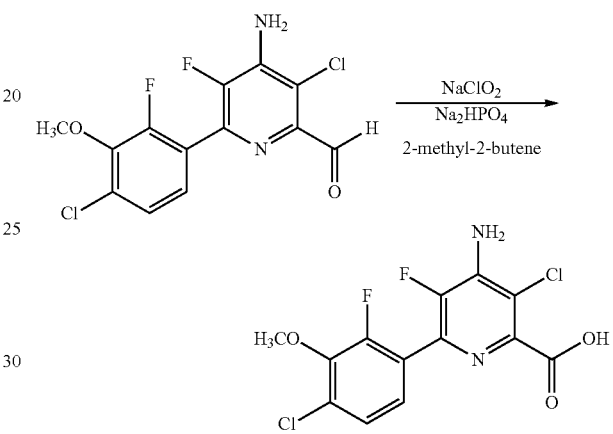

A 25 mL round bottom flask equipped with a magnetic stir bar and reflux condenser was charged with 4-amino-3-chloro-6-(4-chloro-2-fluoro-3-methoxyphenyl)-5-fluoropyridine-2-carbaldehyde (400 mg, 1.201 mmol) and t-butanol (6 mL). Rapid stirring and warming with a heat gun failed to dissolved all of the aldehyde. Additional t-butanol (2 mL) was added, but still failed to form a homogeneous solution. The mixture was treated with H$_2$O (2 mL), 2-methyl-2-butene (1 mL), sodium phosphate dibasic dihydrate (Na$_2$HPO$_4$; 341 mg, 2.402 mmol, 2 equiv) and finally sodium chlorite (326 mg, 3.60 mmol, 3 equiv) was added in one portion. The mixture was stirred at room temperature for 5 min and then placed in an oil bath and heated to 85° C. After stirring at 85° C. for 60 min, the reaction mixture finally became a light yellow, homogenous solution. After stirring at 83° C. overnight (12 h), an aliquot of the reaction mixture was partitioned between EtOAc and 1 molar (M) hydrochloric acid (HCl) and analyzed by HPLC and LC-MS. HPLC analysis showed that all of the starting material had been consumed and one major, slightly more polar product formed along with multiple minor products. LC-MS analysis showed one major product with the correct mass for the desired product. The reaction mixture was allowed to cool to room temperature, diluted with EtOAc (15 mL) and washed with 1 M HCl (1×5 mL), H$_2$O (1×5 mL) and saturated NaCl (1×5 mL). HPLC analysis of the combined aqueous washes showed only trace amounts of the desired product. The organic phase was dried (Na$_2$SO$_4$), filtered and concentrated in vacuo to give 414 mg of a cream-colored solid. The crude material was stirred with Et$_2$O (5 mL). After stirring for 3 h, the solid was removed by vacuum filtration washing with Et$_2$O. The solid was air-dried for several hours and then dried under vacuum. The title compound (348 mg, 83%) was isolated as a white solid: $^1$H NMR (400 MHz, DMSO-$d_6$) δ 13.66 (s, 1H), 7.47 (dd, J=8.5, 1.4 Hz, 1H), 7.31 (dd, J=8.4, 7.1 Hz, 1H), 7.04 (s, 2H), 3.93 (s, 4H); $^{19}$F NMR (376 MHz, DMSO-$d_6$) δ −129.10 (d, J=28.3 Hz), −138.56 (d, J=28.4 Hz); ESIMS m/z 349 ([M+H]$^+$), 347 ([M−H]$^−$).

Example 17

4-Amino-3-chloro-6-(4-chlorophenyl)-5-fluoropicolinic acid

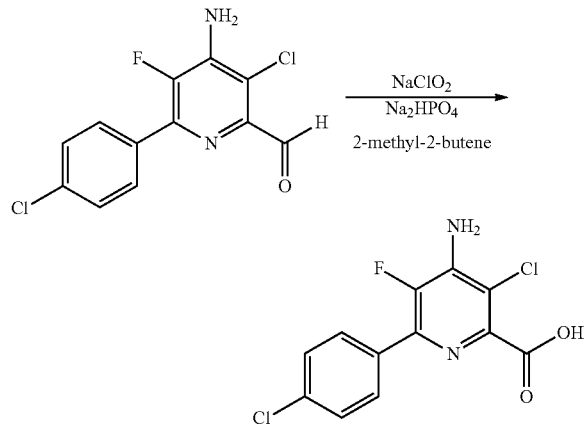

4-Amino-3-chloro-6-(4-chlorophenyl)-5-fluoropicolinaldehyde (105 mg, 0.37 mmol) was dissolved in t-butanol (2.2 mL). Water (800 µL), 2-methyl-2-butene (1.0 mL, 700 mg, 10 mmol), disodium hydrogen phosphate (276 mg, 2 mmol) and sodium chlorite (106 mg, 1.2 mmol) were added to a crimp seal microwave vial. The reactants were mixed, and the reaction vessel sealed and heated to 80° C. for 16 h. The reaction mixture was then cooled to ambient temperature and the mixture diluted with 1 N HCl (5 mL) and EtOAc (10 mL). After stiffing for 5 min, the layers were separated, and the aqueous layer was extracted with EtOAc (4×5 mL). The combined organic layers were dried (Na$_2$SO$_4$) and evaporated to dryness to provide 95 mg of an oily brown solid. The solid was dissolved in a minimum of aqueous 1 N sodium hydroxide (NaOH) and slowly neutralized with aqueous 4 N HCl until a white/brown precipitate appeared. The precipitate was collected and dried, yielding 4-amino-3-chloro-6-(4-chlorophenyl)-5-fluoropicolinic acid (78 mg, 72%): $^1$H NMR (400 MHz, CDCl$_3$) δ 8.5 (br s, 1H), 7.96-7.86 (m, 2H), 7.59-7.75 (m, 2H), 6.1 (br s, 2H); $^{19}$F NMR (376 MHz, DMSO-$d_6$) δ −141.07; ESIMS m/z 299. 4 ([M−H]$^−$).

Example 18

4-Amino-3-chloro-6-propyl-5-fluoropicolinic acid

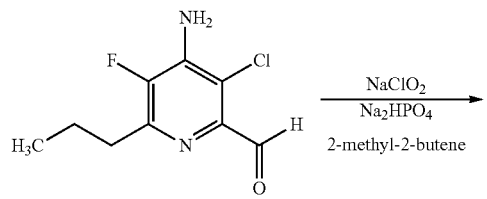

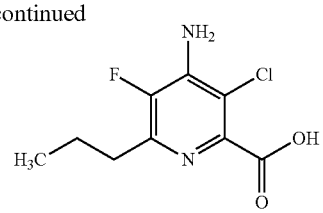

A microwave vial equipped with a magnetic stir bar was charged with 4-amino-3-chloro-6-propyl-5-fluoropicolinaldehyde (15.9 mg, 0.072 mmol) and t-butanol (1.0 mL). The mixture was treated with H$_2$O (0.40 mL), 2-methylbut-2-ene (100 µL, 0.10 mmol), sodium hydrogenphosphate (21.6 mg, 0.100 mmol), and finally sodium chlorite (19.28 mg, 0.206 mmol) was added in one portion. The mixture was heated to 85° C. for 16 h. An aliquot of the reaction mixture was analyzed by LC-MS. LC-MS analysis showed one major product with the correct mass for the desired product. The reaction mixture was evaporated to dryness under N$_2$. Purification via reverse phase chromatography yielded 4-amino-3-chloro-6-propyl-5-fluoropicolinic acid (4.7 mg, 27.9%): $^1$H NMR (400 MHz, CDCl$_3$) δ 11.60 (s, 1H), 4.98 (m, 2H), 2.76 (m, 2H), 1.75 (m, 2H), 0.99 (m, 3H); $^{19}$F NMR (376 MHz, CDCl$_3$) δ−139.98; ESIMS m/z 231.2 ([M−H]$^−$).

Example 19

4-Amino-6-(tert-butyl)-3-chloro-5-fluoropicolinic acid

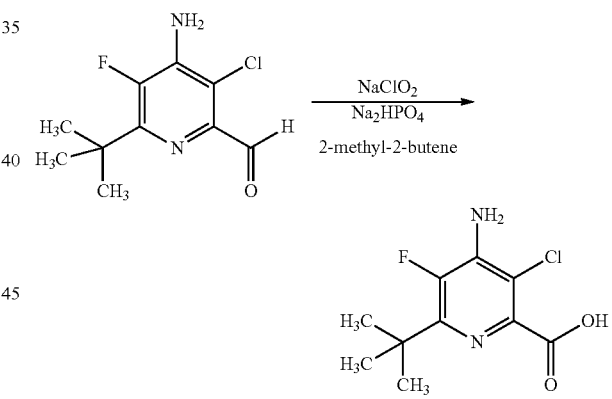

A microwave vial equipped with a magnetic stir bar was charged with 4-amino-6-(tert-butyl)-3-chloro-5-fluoropicolinaldehyde (316 mg, 1.370 mmol) and t-butanol (6.85 mL). The mixture was treated with H$_2$O (2.283 mL), 2-methylbut-2-ene (1.1 mL, 1.370 mmol), sodium hydrogenphosphate (389 mg, 2.74 mmol). Finally, sodium chlorite (372 mg, 4.11 mmol) was added in one portion. The mixture was heated to 70° C. in the microwave for 2 h. An aliquot of the reaction mixture was analyzed by LC-MS. LC-MS analysis showed one major product with the correct mass for the desired product. The reaction mixture was diluted with EtOAc (15 mL) and washed with 1 M HCl (1×5 mL), H$_2$O (1×5 mL) and saturated NaCl (1×5 mL). HPLC analysis of the combined aqueous washes showed only trace amounts of the desired product. The organic phase was dried (Na$_2$SO$_4$), filtered and concentrated in vacuo to give 414 mg of a cream colored solid. The crude material was stirred with Et$_2$O (~5 mL). After stirring for ~3 h the solid was removed by vacuum filtration washing with Et₂O. The solid was air-dried for several hours and then dried under vacuum. The title compound (348 mg, >99%) was isolated as a white solid: mp 149-151° C.; ¹H NMR (400 MHz, CDCl₃) δ 11.60 (s, 1H), 4.97 (s, 2H), 1.41 (d, J=1.5 Hz, 9H); ¹⁹F NMR (376 MHz, CDCl₃) δ −132.92; ¹³C NMR (101 MHz, CDCl₃) δ 161.62, 151.12, 149.21, 146.63, 141.58, 117.18, 36.69, 28.37.

Example 20

4-Amino-3-chloro-6-cyclobutyl-5-fluoropicolinic acid

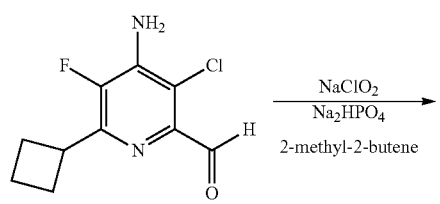

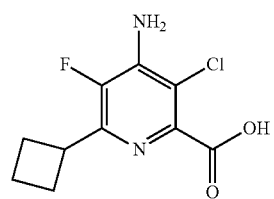

A microwave vial equipped with a magnetic stir bar was charged with 4-amino-3-chloro-6-cyclobutyl-5-fluoropicolinaldehyde (209 mg, 0.914 mmol) and t-butanol (4.57 mL). The mixture was treated with water (1.523 mL), 2-methylbut-2-ene (0.8 mL, 0.914 mmol), sodium hydrogenphosphate (260 mg, 1.828 mmol), and finally sodium chlorite (248 mg, 2.74 mmol) was added in one portion. The mixture was heated to 70° C. in the microwave for 2 h. After stirring at room temperature overnight, an aliquot of the reaction mixture was analyzed by LC-MS. LC-MS analysis showed one major product with the correct mass for the desired product. The reaction mixture was diluted with EtOAc (15 mL) and washed with 1 M HCl (1×5 mL), H₂O (1×5 mL) and saturated NaCl (1×5 mL). The organic phase was dried (Na₂SO₄), filtered and concentrated in vacuo. The crude residue was triturated with Et₂O and the Et₂O removed giving 4-amino-3-chloro-6-cyclobutyl-5-fluoropicolinic acid (94 mg, 39.9%) as a yellow solid: ¹H NMR (400 MHz, CDCl₃) 11.60 (s, 1H), δ 4.94 (d, J=18.2 Hz, 2H), 3.86 (ttdd, J=9.1, 8.2, 2.1, 1.0 Hz, 1H), 2.35 (dddd, J=13.1, 6.9, 3.4, 1.8 Hz, 3H), 2.12 (m, 2H), 1.95 (m, 2H); ¹⁹F NMR (376 MHz, CDCl₃) δ −140.30; ESIMS m/z 243 ([M−H]⁻).

Example 20

4-Amino-3-chloro-6-(cyclopropylmethyl)-5-fluoropicolinic acid

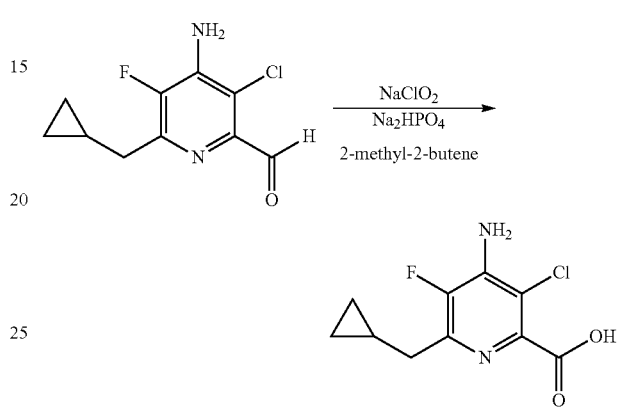

A microwave vial equipped with a magnetic stir bar was charged with 4-amino-3-chloro-6-(cyclopropylmethyl)-5-fluoropicolinaldehyde (63 mg, 0.276 mmol) and t-butanol (1.378 mL). The mixture was treated with H₂O (0.459 mL), 2-methylbut-2-ene (0.3 mL, 0.276 mmol), sodium hydrogenphosphate (78 mg, 0.551 mmol), and finally sodium chlorite (74.8 mg, 0.827 mmol) was added in one portion. The mixture was heated to 70° C. in the microwave for 2 h. An aliquot of the reaction mixture was analyzed by LC-MS. LC-MS analysis showed one major product with the correct mass for the desired product. The reaction mixture was evaporated to dryness under N₂. Purification via reverse phase chromatography yielded 4-amino-3-chloro-6-(cyclopropylmethyl)-5-fluoropicolinic acid (6.2 mg, 9.5%); ¹H NMR (400 MHz, CDCl₃) δ 11.60 (s, 1H), 5.00 (m, 2H), 2.70 (dd, J=7.0, 2.6 Hz, 2H), 1.17-1.02 (m, 1H), 0.60-0.48 (m, 2H), 0.27 (m, 2H); ¹⁹F NMR (376 MHz, CDCl₃) δ −139.97; ESIMS m/z 243.2 ([M−H]⁻).

Example 21

4-Amino-3-chloro-5-fluoro-6-(4-fluorobenzyl)picolinic acid

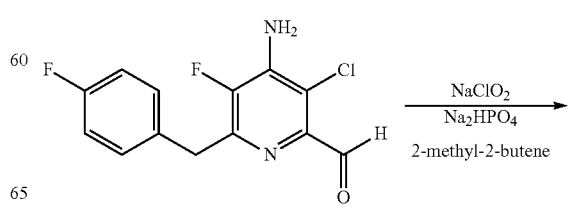

-continued

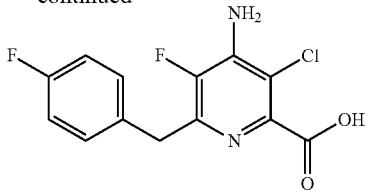

A microwave vial equipped with a magnetic stir bar was charged with 4-amino-3-chloro-5-fluoro-6-(4-fluorobenzyl)picolinaldehyde (280 mg, 0.991 mmol) and t-butanol (4.95 mL). The mixture was treated with H$_2$O (1.651 mL), 2-methylbut-2-ene (0.94 mL, 0.991 mmol), sodium hydrogenphosphate (281 mg, 1.981 mmol), and finally sodium chlorite (269 mg, 2.97 mmol) was added in one portion. The mixture was heated to 70° C. in the microwave for 2 h. An aliquot of the reaction mixture was analyzed by LC-MS. LC-MS analysis showed one major product with the correct mass for the desired product. The reaction mixture was diluted with EtOAc (15 mL) and washed with 1 M HCl (1×5 mL), H$_2$O (1×5 mL) and saturated NaCl (1×5 mL). The organic phase was dried (Na$_2$SO$_4$), filtered and concentrated in vacuo. The crude material was stirred with Et$_2$O (5 mL). After stiffing, the solid was removed by vacuum filtration washing with Et$_2$O. The solid was air-dried for several hours and then dried under vacuum. 4-Amino-3-chloro-5-fluoro-6-(4-fluorobenzyl)picolinic acid (40 mg, 12.84%) was isolated as an off-white solid: $^1$H NMR (400 MHz, CDCl$_3$) δ 11.60 (s, 1H), 7.22 (m, 2H), 7.00 (m, 2H), 5.03 (s, 2H), 4.08 (m, 2H); $^{19}$F NMR (376 MHz, CDCl$_3$) δ −115.76, −139.38; ESIMS m/z 297 ([M−H]$^−$).

Example 22

Benzyl 4-amino-3-chloro-6-(4-chloro-2-fluoro-3-methoxyphenyl)-5-fluoropyridine-2-carboxylate

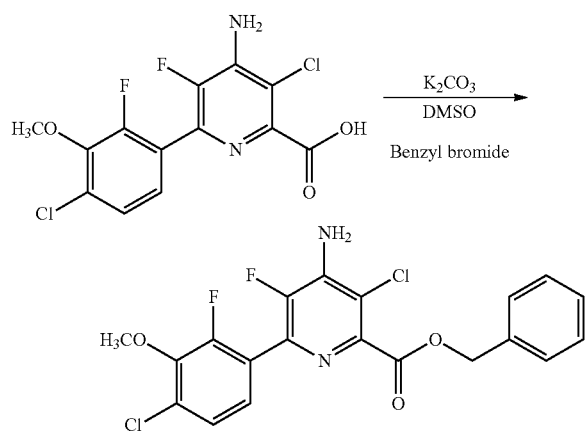

A 50 mL round bottom flask containing a magnetic stir bar was charged with 4-amino-3-chloro-6-(4-chloro-2-fluoro-3-methoxyphenyl)-5-fluoropyridine-2-carboxylic acid (519 mg, 1.487 mmol) and anhydrous DMSO (10 mL). To this solution was added powdered potassium carbonate (K$_2$CO$_3$, 325 mesh; 311 mg, 2.97 mmol, 2.0 equiv) followed by benzyl bromide (0.23 mL, 1.933 mmol, 1.3 equiv). The resultant mixture was stirred at room temperature under an atmosphere of N$_2$. After stirring overnight (17 h) an aliquot of the reaction mixture was partitioned between 1 M HCl and EtOAc and analyzed by HPLC and TLC. HPLC analysis showed that essentially all of the starting carboxylic acid had been consumed (~0.5% remaining) The reaction mixture was diluted with EtOAc (30 mL) and washed with H$_2$O (3×10 mL) and saturated NaCl (1×10 mL). The organic phase was dried (Na$_2$SO$_4$), filtered and concentrated in vacuo to give 0.72 g of a light yellow solid. The crude material was dissolved in CH$_2$Cl$_2$ (2 mL), loaded onto a silica gel column and purified by chromatography using the following setup: Teledyne-Isco CombiFlash Companion, 24 g RediSep silica gel column, flow=40 mL/min, detection at 254 nm, solvent A=hexanes, solvent B=EtOAc. A linear gradient was used starting at 100% A (1 min) and going to 75% B over a period of 10 min Fractions containing clean, desired product were combined and concentrated in vacuo. The title compound (593 mg, 91%) was isolated as a white solid: $^1$H NMR (400 MHz, CDCl$_3$) δ 7.50-7.42 (m, 2H), 7.42-7.31 (m, 3H), 7.26 (d, J=3.6 Hz, 2H), 5.43 (s, 2H), 4.92 (s, 2H), 3.98 (d, J=1.2 Hz, 3H); $^{19}$F NMR (376 MHz, CDCl$_3$) δ−128.20 (d, J=32.8 Hz), −137.74 (d, J=34.5 Hz); ESIMS m/z 439 ([M+H]$^+$), 437 ([M−H]$^−$).

Example 23

2-(4-Chlorophenyl)-6-(diethoxymethyl)-N-tritylpyridin-4-amine

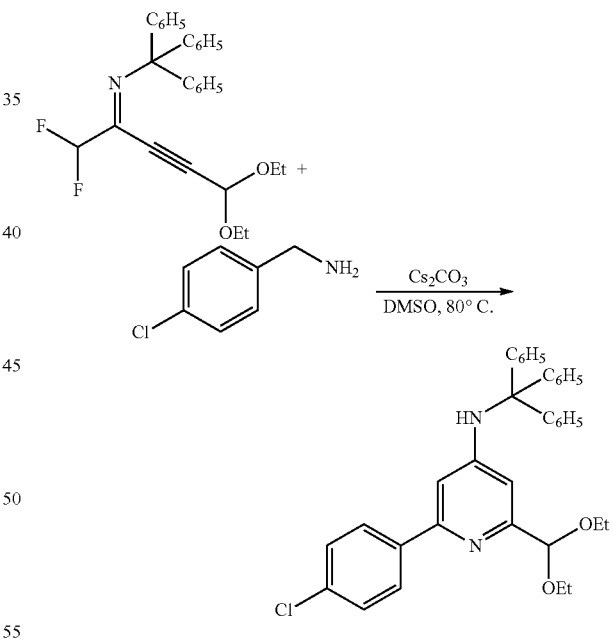

A 25 mL round bottom flask equipped with a magnetic stir bar and reflux condenser was charged with the N-(5,5-diethoxy-1,1-difluoropent-3-yn-2-ylidene)-1,1,1-triphenylmethanamine (0.885 g, 2 mmol) and anhydrous DMSO (Aldrich Sure/Seal™; 10 mL). Once all of the alkyne had dissolved 4-chlorobenzylamine (0.73 mL, 6 mmol) was added followed by cesium carbonate (1.63 g, 5 mmol). The solution went from light yellow to dark green in color. The resultant mixture was placed in an oil bath that had been pre-heated to 80° C. After stirring at 80° C. for 2 h, an aliquot of the reaction mixture was partitioned between EtOAc and H₂O and analyzed by TLC (90/10 hexanes/EtOAc). TLC analysis indicated that all of the alkyne starting material had been consumed.

The reaction mixture was allowed to cool to room temperature, diluted with EtOAc (75 mL) and washed with H₂O (3×25 mL) and saturated NaCl (1×25 mL). The organic phase was dried (Na₂SO₄), filtered and concentrated in vacuo to give 1.88 g of a yellow oil. The crude material was dissolved in hexanes and a minor amount of EtOAc, loaded onto a silica gel column and purified by chromatography using the following setup: Teledyne-Isco CombiFlash Companion, 80 g RediSep silica gel column, flow=60 mL/min, detection at 254 nm, solvent A=hexanes, solvent B=EtOAc. A linear gradient was used starting at 100% A (3 min) and going to 30% B over a period of 20 min Fractions containing clean major product were combined and concentrated in vacuo to give 0.590 g of a dark yellow, viscous oil. The residue was treated with hexanes and concentrated (multiple times) to give 2-(4-chlorophenyl)-6-(diethoxymethyl)-N-tritylpyridin-4-amine (0.540 g, 49%) as a tan foam: ¹H NMR (400 MHz, CDCl₃) δ 7.46 (d, J=8.5 Hz, 2H), 7.35-7.20 (m, 17H), 6.67 (d, J=1.8 Hz, 1H), 6.35 (s, 1H), 5.58 (s, 1H), 5.31 (s, 1H), 3.69-3.58 (m, 2H), 3.57-3.46 (m, 2H), 1.20 (t, J=7.1 Hz, 6H); IR (thin film) 3471, 3057, 2972, 2871, 1597, 1488, 1445, 1089, 1058 cm⁻¹; HRMS-ESI m/z ([M+H]⁺) calcd for $C_{35}H_{33}ClN_2O_2$, 548.2231. found, 548.2238.

Example 24

4-Amino-6-(4-chlorophenyl)pyridine-2-carbaldehyde

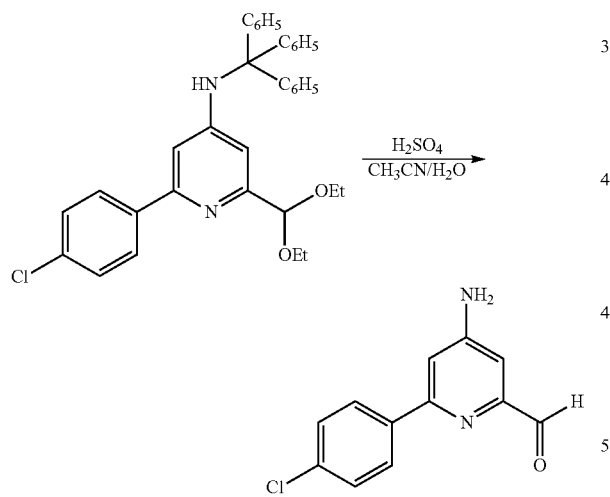

A mixture of the 2-(4-chlorophenyl)-6-(diethoxymethyl)-N-tritylpyridin-4-amine (194 mg, 0.35 mmol) in CH₃CN (2 mL) and H₂O (2 mL) was treated with 1 M H₂SO₄ (1 mL). The resultant solution was placed in an oil bath that had been pre-heated to 80° C. After 90 min at 80° C., an aliquot of the reaction mixture was partitioned between EtOAc and 10% NaHCO₃ and analyzed by TLC (80/20 hexanes/EtOAc) and HPLC. Analysis showed that all of the starting material had been consumed. However, by HPLC analysis it appears that there is still intermediate present (acetal with trityl group removed, ~17%). After stirring at reflux for an additional 60 min (2.5 h total), HPLC analysis still showed ~8% of the intermediate present. The reaction mixture was heated at 80° C. for an additional 90 min (4 h total) and then allowed to cool to room temperature and filtered through a 0.45 µm Whatman PTFE filter disc (to remove trityl alcohol).

The filtrate was neutralized with 10% NaHCO₃ and extracted with EtOAc (3×10 mL). The combined EtOAc extracts were washed with H₂O (1×10 mL), saturated NaCl (1×10 mL), dried (Na₂SO₄), filtered and concentrated in vacuo to give 93 mg of a tan oil. The crude material was dissolved in CH₂Cl₂, loaded onto a silica gel column and purified by chromatography using the following setup: Teledyne-Isco CombiFlash Companion, 12 g RediSep silica gel column, flow=30 mL/min, detection at 254 nm, solvent A=hexanes, solvent B=EtOAc. A linear gradient was used starting at 100% A (1 min) and going to 100% B over a period of 11 min. 4-Amino-6-(4-chlorophenyl)pyridine-2-carbaldehyde (46 mg, 56%) was isolated as a light yellow solid: ¹H NMR (400 MHz, CDCl₃) δ 10.04 (s, 1H), 7.99-7.87 (m, 2H), 7.48-7.40 (m, 2H), 7.15 (d, J=2.2 Hz, 1H), 7.09 (d, J=2.2 Hz, 1H), 4.44 (s, 2H); HRMS-ESI m/z ([M+H]⁺) calcd for $C_{12}H_9ClN_2O$, 232.0403. found, 232.0408.

Example 25

N-tert-Butyl-2-(4-chlorophenyl)-6-(diethoxymethyl)-3-fluoropyridin-4-amine

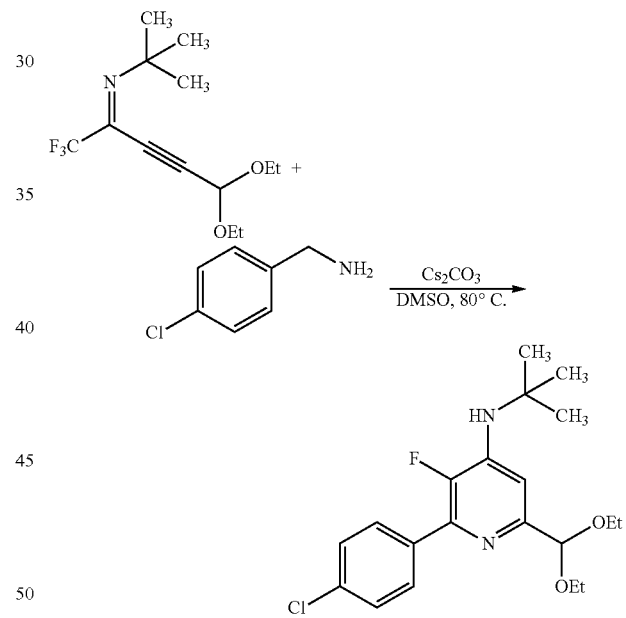

A 100 mL round bottom flask containing a magnetic stir bar was charged with the N-tert-butyl-2,2,2-trifluoroethanimidoyl chloride (2.50 g, 8.95 mmol), 4-chlorobenzylamine (3.3 mL, 26.9 mmol), DMSO (45 mL) and finally cesium carbonate (7.29 g, 22.4 mmol). The resultant mixture was heated to 80° C. under an atmosphere of N₂. After stirring at 80° C. for 90 min, an aliquot of the reaction mixture was partitioned between EtOAc and H₂O and analyzed by TLC (80/20 hexanes/EtOAc). TLC analysis indicated that all of the alkyne starting material had been consumed and one major product formed.

The reaction mixture was allowed to cool to room temperature, diluted with EtOAc (150 mL) and washed with H₂O (3×50 mL) and saturated NaCl (1×50 mL). The organic phase was dried (Na₂SO₄), filtered and concentrated in vacuo to give 4.93 g of a dark yellow oil. The crude material was dissolved in hexanes, loaded onto a silica gel column and purified by chromatography using the following method: Teledyne-Isco CombiFlash Companion, 120 g RediSep silica gel column, flow=85 mL/min, detection at 254 nm, solvent A=hexanes, solvent B=EtOAc. The following stepwise gradient was used: 100% A (5 min), 95% A/5% B (5 min), 90% A/10% B (5 min), 85% A/15% B (5 min), 80% A/20% B (5 min), 75% A/25% B (5 min) and finally 70% A/30% B (5 min). Fractions containing "clean" major product were combined and concentrated in vacuo. N-tert-Butyl-2-(4-chlorophenyl)-6-(diethoxymethyl)-3-fluoropyridin-4-amine (2.987 g, 88%) was isolated as an amber oil: $^1$H NMR (400 MHz, CDCl$_3$) δ 7.83 (dd, J=8.6, 1.5 Hz, 2H), 7.40 (d, J=8.6 Hz, 1H), 7.10 (d, J=6.4 Hz, 1H), 5.33 (s, 1H), 4.56 (d, J=5.1 Hz, 1H), 3.77 (dq, J=9.4, 7.0 Hz, 2H), 3.62 (dq, J=9.5, 7.0 Hz, 2H), 1.46 (s, 9H), 1.27 (t, J=7.1 Hz, 6H); $^{19}$F NMR (376 MHz, CDCl$_3$) δ −150.71 (t, J=5.7 Hz); EIMS m/z 380 (M$^+$), 379, 336, 307, 291, 251, 236, 223, 186, 103, 75, 57.

Example 26

4-Amino-6-(4-chlorophenyl)-5-fluoropyridine-2-carbaldehyde

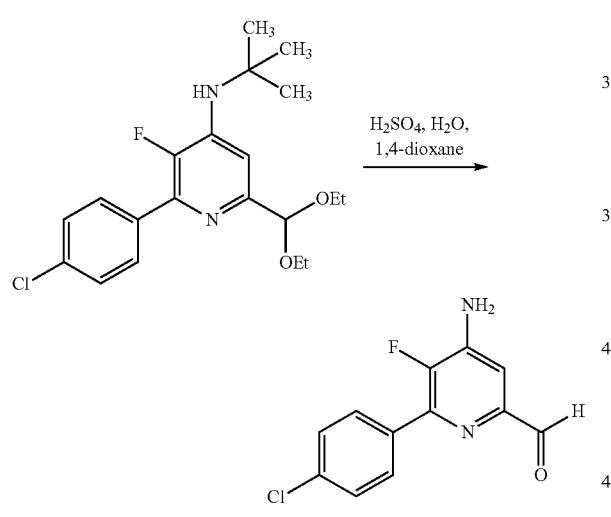

A 25 mL round bottom flask was charged with the N-tert-butyl-2-(4-chlorophenyl)-6-(diethoxymethyl)-3-fluoropyridin-4-amine (250 mg, 0.67 mmol), 1,4-dioxane (10 mL) and 6 M H$_2$SO$_4$ (1 mL). The resultant cloudy looking mixture was allowed to stir at room temperature under an atmosphere of N$_2$. After stirring overnight (~16 h) at room temperature, an aliquot of the reaction mixture was partitioned between 1 M HCl and EtOAc and analyzed by HPLC. HPLC analysis showed only starting material present. The reaction mixture was heated to 80° C. The temperature actually went up to 100° C. due to the temperature probe not being all the way down into the heating block. After stiffing at 80-100° C. for 2 h, HPLC analysis indicated that all of the starting material had been consumed and only a trace of the intermediate 4-N-t-butylpyridine-2-carboxaldehyde was present (mainly desired product, >75%).

The reaction mixture was allowed to cool to room temperature, diluted with EtOAc and cautiously treated with an aqueous solution of NaHCO$_3$ (1.5 g in 15 mL H$_2$O). The phases were separated, and the organic phase was washed with H$_2$O (1×10 mL) and saturated NaCl (1×10 mL), dried (Na$_2$SO$_4$) filtered and concentrated to give 149 mg of a tan solid. The crude material was dissolved in a mixture of CH$_2$Cl$_2$ and EtOAc, loaded onto a silica gel column and purified by chromatographed using the following method: Teledyne-Isco CombiFlash Companion, 24 g RediSep silica gel column, flow=40 mL/min, detection at 254 nm, solvent A=hexanes, solvent B=EtOAc. The following gradient was used: starting at 100% A (1 min) and going to 85% A/15% B over a period of 2 min (linear); held at 85% A for 3 min then to 50% A/50% B over a period of 6 min (linear); and held at 50% A for 5 min. 4-Amino-6-(4-chlorophenyl)-5-fluoropyridine-2-carbaldehyde (88 mg, 54%) was isolated as a white solid: $^1$H NMR (400 MHz, CDCl$_3$) δ 9.95 (s, 1H), 8.09-7.80 (m, 2H), 7.53-7.45 (m, 2H), 7.33 (d, J=6.4 Hz, 1H), 4.55 (s, 2H); $^{19}$F NMR (376 MHz, CDCl$_3$) δ −142.53; EIMS m/z 250 (M$^+$), 221, 187, 167, 158, 140, 133, 94, 75.

Example 27

4-(tert-Butylamino)-6-(4-chlorophenyl)-5-fluoropyridine-2-carbaldehyde

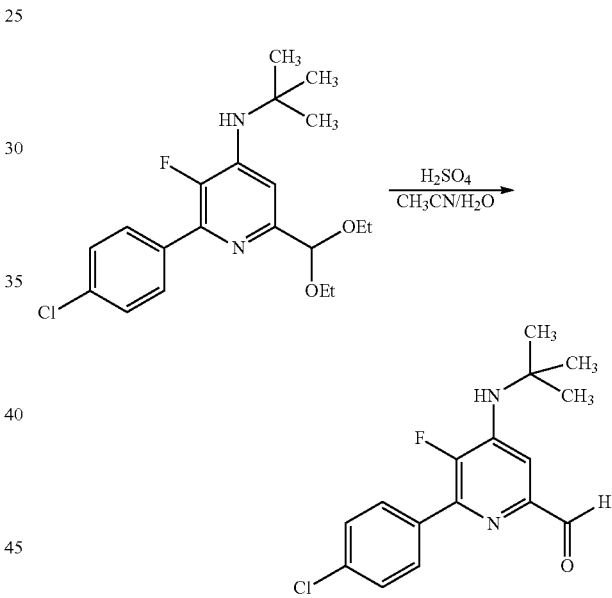

A mixture of the N-tert-butyl-2-(4-chlorophenyl)-6-(diethoxymethyl)-3-fluoropyridin-4-amine (130 mg, 0.34 mmol) in CH$_3$CN (1 mL) and H$_2$O (1 mL) was treated with 1 M H$_2$SO$_4$ (0.5 mL) resulting in a light yellow solution. The reaction flask was placed in an oil bath and heated to 78° C. After 4 h, an aliquot of the reaction mixture was partitioned between EtOAc and 10% NaHCO$_3$ and analyzed by HPLC. HPLC analysis showed that all of the starting material had been consumed and only a trace of the desired product formed (mainly aldehyde with t-butylamine still intact). After stirring for 20 h at 78° C., HPLC analysis still showed only a trace of the desired product (<2%). The reaction was stopped at this point.

The reaction mixture was allowed to cool to room temperature, diluted with EtOAc (15 mL) and washed with 10% NaHCO$_3$ (1×5 mL) and saturated NaCl (1×5 mL). The organic phase was dried (Na$_2$SO$_4$), filtered and concentrated in vacuo to give 113 mg of a brown solid. The crude material was dissolved in hexanes, loaded onto a silica gel column and purified by chromatography using the following setup: Teledyne-Isco CombiFlash Companion, 12 g RediSep silica gel column, flow=30 mL/min, detection at 254 nm, solvent A=hexanes, solvent B=EtOAc. A linear gradient was used starting at 100% A (1 min) and going to 60% B over a period of 12 min. Fractions containing the major product were combined and concentrated in vacuo. 4-(tert-Butylamino)-6-(4-chlorophenyl)-5-fluoropyricolinaldehyde (85 mg, 81%) was isolated as a light tan solid: $^1$H NMR (400 MHz, CDCl$_3$) δ 9.95 (s, 1H), 7.96-7.87 (m, 2H), 7.52-7.40 (m, 3H), 4.72 (d, J=4.8 Hz, 1H), 1.50 (s, 9H); $^{19}$F NMR (376 MHz, CDCl$_3$) δ −142.42 (s); HRMS-ESI m/z ([M+H]$^+$) calcd for C$_{16}$H$_{16}$ClFN$_2$O, 306.0935. found, 306.0933.

What is claimed is:

1. A process for the preparation of a 4-amino-3-halo-6-(substituted)picolinate of the Formula I

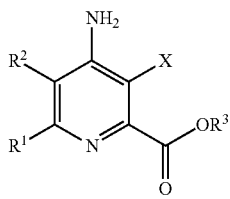

I wherein

X represents Cl, Br or I,

R$^1$ represents H, C$_1$-C$_6$ alkyl, C$_3$-C$_6$ cycloalkyl, C$_4$-C$_6$ cycloalkylalkyl, C$_3$-C$_6$ heterocycle, C$_2$-C$_4$ alkenyl or phenyl, arylalkyl or heteroarylalkyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy, R$^2$ represents H or F, and R$^3$ represents C$_1$-C$_{12}$ alkyl or an unsubstituted or substituted C$_7$-C$_{11}$ arylalkyl, which comprises the following steps:

a) contacting difluoroacetic acid or trifluoroacetic acid with tritylamine or t-butylamine in the presence of a triarylphosphine and a trialkylamine base in carbon tetrachloride solvent to produce a 2,2-difluoro- or 2,2,2-trifluoro-N-(trityl or t-butyl)ethanimidoyl chloride (Formula A)

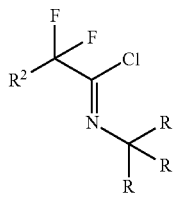

A wherein each R represents CH$_3$ or each R represents C$_6$H$_5$, and R$^2$ represents H or F;

b) contacting the 2,2-difluoro- or 2,2,2-trifluoro-N-(trityl or t-butyl)ethanimidoyl chloride (Formula A) with a 3,3-dialkoxyprop-1-yne (Formula B)

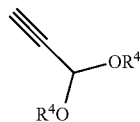

B wherein R$^4$ represents C$_1$-C$_4$ alkyl, in the presence of copper(I) iodide, an alkali metal iodide and an alkali metal phosphate in a polar aprotic solvent to produce an (imino)pent-2-yne dialkyl acetal of Formula C

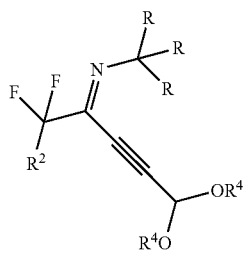

C wherein R, R$^2$ and R$^4$ are as previously defined;

c) cyclizing the (imino)pent-2-yne dialkyl acetal of Formula C with an amine of Formula D

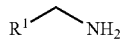

D wherein R$^1$ represents H, C$_1$-C$_6$ alkyl, C$_3$-C$_6$ cycloalkyl, C$_4$-C$_6$ cycloalkylalkyl, C$_3$-C$_6$ heterocycle, C$_2$-C$_4$ alkenyl or phenyl, arylalkyl or heteroarylalkyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy, in the presence of an inorganic alkali metal base in a polar aprotic solvent at a temperature from about ambient to about 100° C. to produce a trityl- or t-butyl-protected 4-amino-6-(substituted)-pyridine-2-dialkyl acetal of Formula E

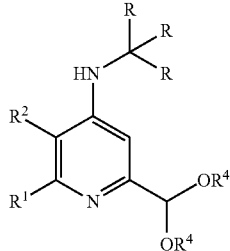

E wherein R, R$^1$, R$^2$ and R$^4$ are as previously defined;

d) deprotecting and hydrolyzing the trityl- or t-butyl-protected 4-amino-6-(substituted) pyridine-2-dialkyl acetal of the Formula E with a mineral acid in a polar solvent to produce the 4-amino-6-(substituted)picolinaldehyde of the Formula F

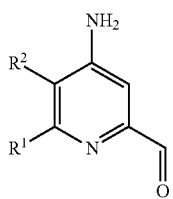

F wherein R$^1$ and R$^2$ are as previously defined;
e) oxidizing the 4-amino-6-(substituted)picolinaldehyde of the Formula F with an alkali metal chlorite in the presence of an inorganic acid and a hypochlorous acid scavenger in an aqueous alcoholic solvent to produce a 4-amino-6-(substituted)picolinic acid of the Formula G

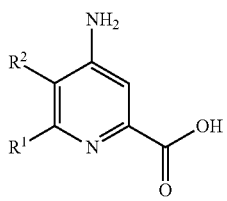

G wherein R$^1$ and R$^2$ are as previously defined;
f) esterifying the 4-amino-6-(substituted)picolinic acid of the Formula G with a compound of the formula

R$^3$Y wherein
Y represents OH, Cl, Br, or I, and
R$^3$ represents C$_1$-C$_{12}$ alkyl or an unsubstituted or substituted C$_7$-C$_{11}$ arylalkyl, to produce a 4-amino-6-(substituted)picolinate of Formula H

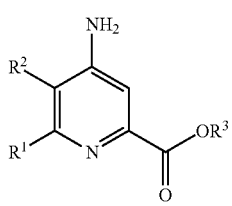

H wherein R$^1$, R$^2$ and R$^3$ are as previously defined; and
g) halogenating the 4-amino-6-(substituted)picolinate of Formula H with a halogen source to produce the 4-amino-3-halo-6-(substituted)picolinate of Formula I.

2. A process for the preparation of a 4-amino-3-halo-6-(substituted)picolinate of the Formula I

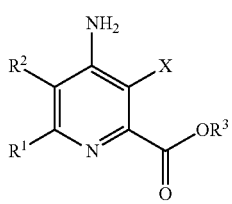

I wherein
X represents Cl, Br or I,
R$^1$ represents H, C$_1$-C$_6$ alkyl, C$_3$-C$_6$ cycloalkyl, C$_4$-C$_6$ cycloalkylalkyl, C$_3$-C$_6$ heterocycle, C$_2$-C$_4$ alkenyl or phenyl, arylalkyl or heteroarylalkyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy,
R$^2$ represents H or F, and
R$^3$ represents C$_1$-C$_{12}$ alkyl or an unsubstituted or substituted C$_7$-C$_{11}$ arylalkyl, which comprises the following steps:
a) contacting difluoroacetic acid or trifluoroacetic acid with tritylamine or t-butylamine in the presence of a triarylphosphine and a trialkylamine base in carbon tetrachloride solvent to produce a 2,2-difluoro- or 2,2,2-trifluoro-N-(trityl or t-butyl)ethanimidoyl chloride (Formula A)

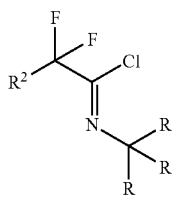

A wherein
each R represents CH$_3$ or each R represents C$_6$H$_5$, and
R$^2$ represents H or F;
b) contacting the 2,2-difluoro- or 2,2,2-trifluoro-N-(trityl or t-butyl)ethanimidoyl chloride (Formula A) with a 3,3-dialkoxyprop-1-yne (Formula B)

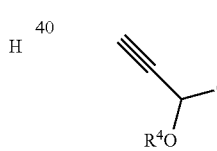

B wherein R$^4$ represents C$_1$-C$_4$ alkyl,
in the presence of copper(I) iodide, an alkali metal iodide and an alkali metal phosphate in a polar aprotic solvent to produce an (imino)pent-2-yne dialkyl acetal of Formula C

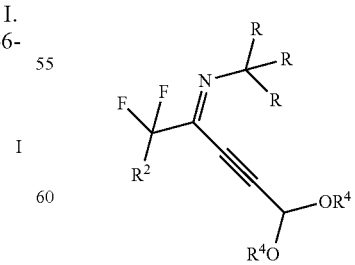

C wherein R, R$^2$ and R$^4$ are as previously defined;
c) cyclizing the (imino)pent-2-yne dialkyl acetal of Formula C with an amine of Formula D

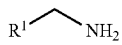

wherein
R¹ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, in the presence of an inorganic alkali metal base in a polar aprotic solvent at a temperature from about ambient to about 100° C. to produce a trityl- or t-butyl-protected 4-amino-6-(substituted)pyridine-2-dialkyl acetal of Formula E

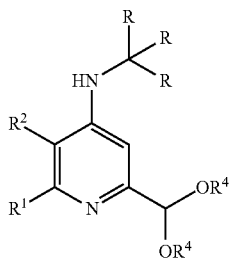

wherein R, R¹, R² and R⁴ are as previously defined;
d) deprotecting and hydrolyzing the trityl- or t-butyl-protected 4-amino-6-(substituted) pyridine-2-dialkyl acetal of the Formula E with a mineral acid in a polar solvent to produce the 4-amino-6-(substituted)picolinaldehyde of the Formula F

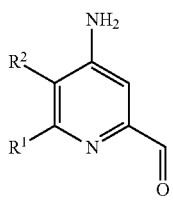

wherein R¹ and R² are as previously defined;
e) halogenating the 4-amino-6-(substituted)picolinaldehyde of Formula F with a halogen source to produce the 4-amino-3-halo-6-(substituted)picolinaldehyde of Formula J

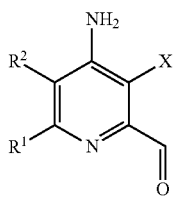

wherein R¹, R² and X are as previously defined;
f) oxidizing the 4-amino-3-halo-6-(substituted)picolinaldehyde of Formula J with an alkali metal chlorite in the presence of an inorganic acid and a hypochlorous acid scavenger in an aqueous alcoholic solvent to produce a 4-amino-3-halo-6-(substituted)picolinic acid of the Formula K

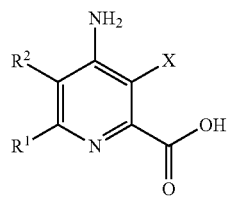

wherein R¹, R² and X are is as previously defined; and
g) esterifying the 4-amino-3-halo-6-(substituted)picolinic acid of the Formula K with a compound of the formula

$R^3Y$ wherein
Y represents OH, Cl, Br, or I, and
R³ represents $C_1$-$C_{12}$ alkyl or an unsubstituted or substituted $C_7$-$C_{11}$ arylalkyl, to produce the 4-amino-3-halo-6-(substituted)picolinate of Formula I.

3. The compound

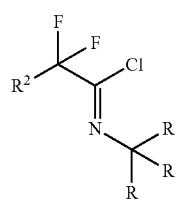

wherein
each R represents $CH_3$ or each R represents $C_6H_5$, and
R² represents H or F.

4. A compound of Formula C

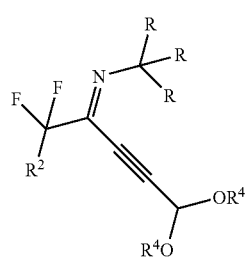

wherein
each R represents $CH_3$ or each R represents $C_6H_5$, and
R² represents H or F, and
R⁴ represents $C_1$-$C_4$ alkyl.

5. A compound of Formula E

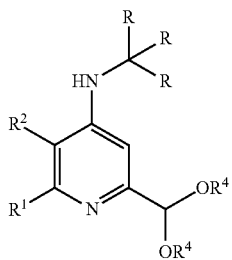

wherein
$R^1$ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy,
each R represents $CH_3$ or each R represents $C_6H_5$,
$R^2$ represents H or F, and
$R^4$ represents $C_1$-$C_4$ alkyl.

6. A compound of Formula F

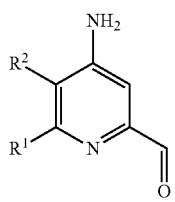

wherein
$R^1$ represents H, $C_1$-$C_6$ alkyl, $C_3$-$C_6$ cycloalkyl, $C_4$-$C_6$ cycloalkylalkyl, $C_3$-$C_6$ heterocycle, $C_2$-$C_4$ alkenyl or phenyl, arylalkyl or heteroarylalkyl, wherein phenyl is optionally substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and
$R^2$ represents H or F.

* * * * *